United States Patent [19]
Falk et al.

[11] Patent Number: 6,022,866
[45] Date of Patent: *Feb. 8, 2000

[54] USE OF HYALURONIC ACID AND FORMS TO PREVENT ARTERIAL RESTENOSIS

[75] Inventors: Rudolf Edgar Falk; Samuel Simon Asculai, both of Toronto; Eva Anne Turley, Winnipeg, all of Canada

[73] Assignee: Hyal Pharmaceutical Corporation, Mississauga, Canada

[*] Notice: This patent is subject to a terminal disclaimer.

[21] Appl. No.: 08/403,766

[22] PCT Filed: Sep. 22, 1993

[86] PCT No.: PCT/CA93/00388

§ 371 Date: Mar. 24, 1995

§ 102(e) Date: Mar. 24, 1995

[87] PCT Pub. No.: WO94/07505

PCT Pub. Date: Apr. 14, 1994

Related U.S. Application Data

[63] Continuation-in-part of application No. 08/285,764, Aug. 3, 1994, Pat. No. 5,614,506, which is a continuation-in-part of application No. 07/952,095, Sep. 28, 1992, abandoned, which is a continuation-in-part of application No. 07/675,908, Jul. 3, 1991, and application No. 07/838,675, Feb. 21, 1992, Pat. No. 5,639,738.

[30] Foreign Application Priority Data

Sep. 25, 1992 [CA] Canada .................................. 2079205

[51] Int. Cl.⁷ .................................................. A61K 31/70
[52] U.S. Cl. ............................... 514/54; 514/23; 514/25; 514/28; 514/32; 514/42; 514/56; 514/60; 514/62; 536/55
[58] Field of Search ............................. 424/180; 514/23, 514/25, 28, 32, 33, 42, 54, 56, 60, 62; 536/55

[56] References Cited

U.S. PATENT DOCUMENTS

| 2,583,096 | 1/1952 | Hadidian et al. . |
| 3,436,454 | 4/1969 | Nouvel . |
| 3,887,703 | 6/1975 | Manoussos et al. . |
| 4,141,973 | 2/1979 | Balazs . |
| 4,272,522 | 6/1981 | Balazs . |
| 4,582,865 | 4/1986 | Balazs et al. . |
| 4,636,524 | 1/1987 | Balazs et al. . |
| 4,707,354 | 11/1987 | Garlen et al. ............................. 424/47 |
| 4,711,780 | 12/1987 | Fahim . |
| 4,716,224 | 12/1987 | Sakurai et al. . |
| 4,725,585 | 2/1988 | Wenge et al. . |
| 4,736,024 | 4/1988 | Della Valle et al. . |
| 4,755,544 | 7/1988 | Makino et al. . |
| 4,795,741 | 1/1989 | Leshchiner et al. . |
| 4,801,619 | 1/1989 | Lindblad . |

(List continued on next page.)

FOREIGN PATENT DOCUMENTS

| 30806/84 | 7/1984 | Australia . |
| 72117/87 | 12/1987 | Australia . |
| 17459/88 | 12/1988 | Australia . |
| 1205031 | 5/1986 | Canada . |
| 1240929 | 8/1988 | Canada . |
| 0138572 | 4/1985 | European Pat. Off. . |
| 0179442 | 4/1986 | European Pat. Off. . |
| 0197718 | 10/1986 | European Pat. Off. . |
| 0208623 | 1/1987 | European Pat. Off. . |
| 0216453 | 4/1987 | European Pat. Off. . |
| 0224987 | 6/1987 | European Pat. Off. . |
| 0240098 | 10/1987 | European Pat. Off. . |
| 0265116 | 4/1988 | European Pat. Off. . |
| 0270317 | 6/1988 | European Pat. Off. . |
| 0285357 | 10/1988 | European Pat. Off. . |

(List continued on next page.)

OTHER PUBLICATIONS

Alaverdyan MI, Ter–Avetisyan AT. Effect of hyaluronidase, hyaluronic acid, and some other substances on postradiational experimental bacteriemai. *Bulletin of Experimental Biology and Medicine* 1967; 64(9): 967–969.

Balazs EA, Band P. Hyaluronic acid: Its structure and use. *Cosmetics & Toiletries* . Polymers in Cosmetics 1984; 99: 65–72.

Balazs EA, Gibbs DA. The rheological properties and biological function of hyaluronic acid. In: *Chemistry and Molecular Biology of the Intercellular Matrix. vol. III.* New York: Academic Press, 1970. pp. 1241–1253.

Balazs EA, B and P. Hyaluronic acid: Its structure and use. *Cosmetics & Toiletries. Polymers in Cosmetics* 1984; 99: 65–72.

Camber O, Edman P, Gurny R. Influence of sodium hyaluronate on the meiotic effect of pilocarpine in rabbits. *Current Eye Research* 1987; 6(6):779–784.

Camber O, Lundgren P. Diffusion of some low molecular weight compounds in sodium hyaluronate. *Acta Pharmaceutica Suecica* 1985; 22(6): 315–320.

Chang N–S. Pro–drug and vehicle approaches to improve the therapeutic index of topically applied timolol in the pigmented rabbit. *Dissertation Abstracts International* 1988; 49(2): 367–B.

Cravioto RO, Massieu GH, Izquierdo JJ. Effects of precipitates formed by insulin with hyaluronic acid and mucoid from vitreous humor in depressing blood–sugar levels. *Science* 1950; 111: 520–521.

(List continued on next page.)

Primary Examiner—Keith D. MacMillan
Attorney, Agent, or Firm—Ivor M. Hughes; Marcelo K. Sarkis; Neil H. Hughes

[57] ABSTRACT

A method is provided of inhibiting the narrowing of the vascular tubular walls of an animal by the proliferation of endothelial cells in the area of trauma after the vascular tubular walls have been traumatized, the method comprising the administration of a therapeutically effective non-toxic amount of a form of hyaluronic acid selected from the group consisting of hyaluronic acid and pharmaceutically acceptable salts thereof to the animal to inhibit the narrowing of the vascular tubular walls by the proliferation of endothelial cells into the area of trauma.

20 Claims, 12 Drawing Sheets

U.S. PATENT DOCUMENTS

| | | |
|---|---|---|
| 4,808,576 | 2/1989 | Schultz et al. . |
| 4,814,176 | 3/1989 | Makino et al. . |
| 4,840,941 | 6/1989 | Ueno et al. . |
| 4,851,521 | 7/1989 | della Valle et al. . |
| 4,853,226 | 8/1989 | Machida et al. . |
| 4,937,254 | 6/1990 | Sheffield et al. . |
| 4,946,870 | 8/1990 | Partain, III et al. . |
| 4,957,744 | 9/1990 | della Valle et al. . |
| 4,965,353 | 10/1990 | della Valle et al. . |
| 4,970,298 | 11/1990 | Silver et al. . |
| 5,032,679 | 7/1991 | Brandley et al. ........................ 536/21 |
| 5,116,864 | 5/1992 | March et al. ........................... 514/455 |
| 5,326,757 | 7/1994 | Demopoulos ........................... 514/167 |

FOREIGN PATENT DOCUMENTS

| | | |
|---|---|---|
| 0287210 | 10/1988 | European Pat. Off. . |
| 0295092 | 12/1988 | European Pat. Off. . |
| 0296740 | 12/1988 | European Pat. Off. . |
| 0378852 | 7/1990 | European Pat. Off. . |
| 57-183707 | 12/1982 | Japan . |
| 61-000017 | 1/1986 | Japan . |
| 61-233622 | 10/1986 | Japan . |
| 116678/88 | 5/1988 | Japan . |
| 63/045223 | 7/1988 | Japan . |
| 1283892 | 8/1972 | United Kingdom . |
| 2099826 | 12/1982 | United Kingdom . |
| 88/07060 | 9/1988 | WIPO . |
| 89/07932 | 9/1989 | WIPO . |
| 91/04058 | 4/1991 | WIPO . |

OTHER PUBLICATIONS

Gieldanowski, Jerzy; Skowronska, Jadwiga Studies on immunosuppressive and anti–inflammatory effect of adriamycin. *Arch. Immunol. Ther. Exp.* (*1980*); 28 (3): 439–446.

Hassan HG, Akerman B, Ranck H, Lindberg B, Lindquist B. Effects of adjuvants to local anaesthetics on their duration Acta Anaesthesiol.

Hurd ER Immunosuppressive and anti–inflammatory properties of cyclophosphamide, azathioprine and methotrexate. *Arthritis and Rheumatism* (*1973*) *Jan.–Feb.*); 16 (1): 84–88.

Idson B. Polymers in skin cosmetics. *Cosmetics & Toiletries* 1988; 103: 63–68.

Johansson A, Hassan H, Renck H. Effects of adjuvants to local anaesthetics on their duration. *Acta Anaesthesiol. Scand.* 1985; 29: 736–738.

Kalbhen DA. The inhibitory effects of steroidal and non–steroidal antirheumatic drugs on articular cartilage in osteo–arthrosis and its counteraction by a biological GAG–peptide complex ("Rumalon"). *Zeitschrift für Rheumatologie* 1982; 41(5): 340–202–211.

Katsu M., Abe T., Shimada S. Significance and clinical use of non–steroid anti–inflammatory drugs as substitutes for steroids in steroid dependence *Nippon Rinsho* (*1968 Jan*); 26(1): 89–95.

Kreis H, Chkoff N, Droz D, et al. Nonsteroid anti–inflammatory agents as a substitute treatment for steroids in ATGAM–treated cadaver kidney recipients.

McIlwraith W. Current concepts in equine degenerative joint disease. *Journal of the American Veterinary Medical Association* 1982; Feb. 1: 239–250.

Mizushima, Y. Possibility of non–steroid anti–inflammatory drugs as a substitute for steroids–analysis of the present situation and demands for the future. *Nippon Rinsho* (*Jan. 1986*); 26(1): 61–65.

Nizolek DJH, White KK. Corticosteroid and hyaluronic acid treatments in equine degenerative joint disease: A review. *The Cornell Veterinarian* 1981; 71(4): 355–375.

Pigman W, et al. Acide hyaluronique et facteurs de perméabilité tissulaire *Bull. Soc. Chim. Biol. 1963*; 45(2–3): 185–202.

Pruett RC, Schepens CL, Constable IJ, Swann DA. Hyaluronic acid vitreous substitute. In: *Vitreous Surgery and Advances in Fundus Diagnosis and Treatment*. Freeman H.M., et al., Editors. Appleton–Century–Crofts, 1977: Chapter 55, pp. 433–444.

Reim M, Teping C. Surgical procedures in the treatment of most severe eye burns. *Acta Ophthalmoligica* 1989–Supplementum 192; 67: 47–54.

Rydell NW, Balazs EA. Effect of intra–articular injection of hyaluronic acid on the clinical symptoms of osteoarthritis and on granulation tissue formation. *Clinical Orthopaedics and Related Research* 1971; 80(Oct.): 25–29.

Saba P, Galeone F, Salvadorini F, Guarguaglini M, Ombrato M. Investigation of the antihyperlipemic activity of an association of clofibrate and extractive mucopolysaccharide complex. *Current Therapeutic Research* 1978; 23(4): 455–463.

Stegman R, Miller D. Use of sodium hyaluronate in severe penetrating ocular trauma. *Acta Ophthalmol.* 1986; 18: 9–13.

Trabucchi E, Foschi D, Marazzi M, Radaelli E, Lucianetti A, Rizzitelli E, Baratti C, et al. Prevention of wound dehiscence in severely obese patients with jejuno–ileal by–pass: The role of hyaluronic acid. *Pharmatherapeutica* 1988; 5(4): 233–239.

Sertoli P, Merello A, Parodi M. L'acido jaluronico, per uso topico, nella cura delle ulcere trofocircolatorie degli arti inferiori. (Comunicazioni). *Giornale Italiano di Dermatologia 1970*; 45(8): 468–471.

Walther, M. The Prevention of Strine Cutis Sistansae During Pregnancy. *Mineva Gynecolgia* (*1981*) *vol. 33*: 497–499.

Weirich, E.G., Longauer, J.K., Kirkwood, A.H. Dermatopharmacology of salicylic acid. III. Topical contra–inflammatory effect of salicylic acid and other drugs in animal experiments. *Dermatologica* (*1976*); 152(2): 87–99.

Sandra Blakeslee, "Solid cores of tumors keeping out best drugs", Jul. 8, 1989 edition of the Globe and Mail, Toronto, Ontario, p. D4.

Pam Harrison, "Toxic drug tamed but still potent" *Ontario Medicine*, vol. 8, No. 16 dated Aug. 21, 1989, p. 1.

*The Merck Index* Eleventh Edition, Centennial Edition, Hyaluronic Acid formulation pp. 751 and 752.

Alan R. Liss, Inc., Modulation of Immunity in Cancer Patients by Prostaglandin Antagonists, *Immunity to Cancer II*.

Goodwin, J.S. Prostaglandin E and Cancer Growth Potential for Immunotherapy with Prostaglandin Synthesis Inhibitors, *Augmentive Agents in Cancer Therapy*, Raven Press, New York, (1981).

Dr. Samuel Asculai, *Inactivation of Herpes Simplex Viruses by Nonionic Surfactants, Antimicrobial Agents and Chemotherapy*, Apr. 1978, pp. 686–690.

Chemical Abstract AN 101: 83760 (Faxon et al, 1984).

Chemical Abstract AN 104: 146248 (Orlidge et al, 1986).

Chemical Abstract AN 1989: 454922, West et al, 1989.

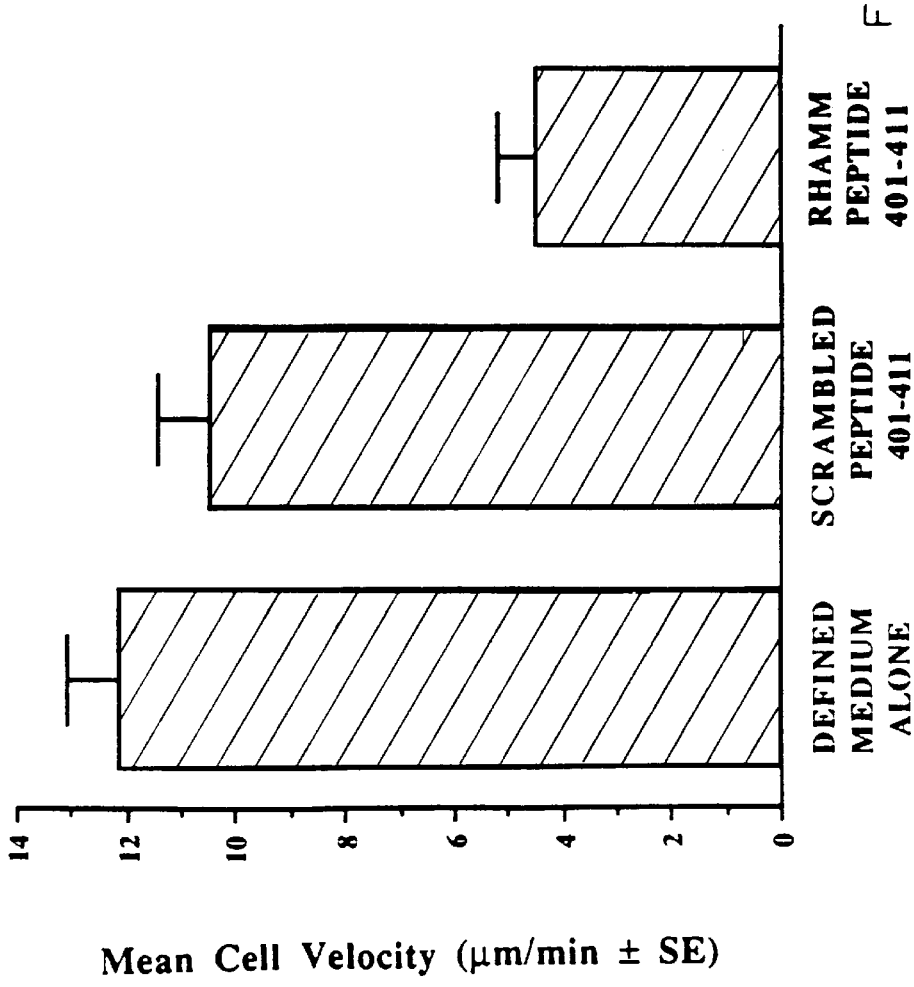

USE OF HYALURONIC ACID AND FORMS TO PREVENT ARTERIAL RESTENOSIS

CROSS-REFERENCE TO RELATED APPLICATIONS

This Application is a Continuation In-Part Application of application Ser. No. 08/285,764 filed on Aug. 03, 1994 U.S. Pat. No. 5,614,506, issued Mar. 25, 1997, wholly incorporated herein by reference which is a Continuation In-Part Application of application Ser. No. 07/952,095 filed on Sep. 28, 1992, abandoned, wholly incorporated herein by reference claiming foreign priority from Canadian Application 2,079,025 filed on Sep. 25, 1992 wherein application Ser. No. 07/952,095 is a Continuation In-Part of application Ser. No. 07/675,908 filed on Jul. 3, 1991 and a Continuation In-Part of application Ser. No. 07/838,675 filed on Feb. 21, 1992 U.S. Pat. No. 5,639,738 issued Jun. 17, 1997 all wholly incorporated herein by reference.

FIELD OF INVENTION

This invention relates to the prevention of the narrowing (stenosis) of tubular walls of an animal after the tubular walls have been traumatized. In one embodiment, this invention relates to the prevention of arterial restenosis after balloon angioplasty.

DESCRIPTION OF THE PRIOR ART

Balloon angioplasty is a widely accepted method of opening blockages in the coronary arteries. The balloon catheter was introduced experimentally in the early 1960's and was first applied clinically in the late 1970's. It has since assumed a major therapeutic role in the treatment of single and multiple vessel coronary artery disease (Baumgartner, H. R., 1963, Z. Ges. Exp. Med., 137:227). However in some patients after successful treatment by balloon angioplasty, arterial restenosis occurs. This time however the narrowing of the inner diameter (ID) of the artery is caused by growth (proliferation) of endothelial cells in the areas of irritation caused by the balloon angioplasty. Thus reblockage occurs not by cholesterol build-up but by build up of endothelial cells on the inner wall of the artery reducing the inner diameter (ID) of the artery leading to an infarct. In man, the restenotic lesion consists almost entirely, though not exclusively of vascular smooth muscle cells (Glazier, J. J., Williams, M. G., Madden, S. and Rickards, A. F., 1990, J. Roy. Coll. Phys. Lond., 24:292). Their accumulation within the artery lumen is a result of cell migration and proliferation. These two events are almost certainly due to the coordinated interaction of a number of different cytokines likely released by early accumulation of macrophages at the site of original tissue injury. This narrowing of the inner diameter (ID) of tubular walls or proliferation of cells is not however restricted or limited to the coronary arteries. It can also occur post operatively causing restenosis in for example peripheral vascular systems.

A number of proposals have been made in the prior art to prevent restenosis.

U.S. Pat. No. 5,087,244 (Wolinsky et al.) purports to teach the use of a catheter having an inelastic balloon at one end thereof, where the balloon has minute perforations and contains a concentrated heparin solution which will be released through the perforations contacting an area of the artery after angioplasty to prevent restenosis.

U.S. Pat. No. 5,116,864 (Hathaway et al.) purports to teach the prevention of restenosis in peripheral or cardiac vascular systems after vascular recanalisation by systemic administration of photo activatable psoralen to give serum psoralen levels which inhibit smooth muscle cell growth.

U.S. Pat. No. 5,092,841 (Spears, J. R.) purports to teach the treatment of an arterial wall injured during angioplasty by delivering bio-protective material between the wall and the angioplasty catheter so that the bio-protective material is entrapped and permeates into the tissues and vessels of the arterial wall during opposition of the angioplasty catheter.

EP 356275-A (Petitou et al.) purports to teach the use of new o-acylated glycosamino-glycan derivatives in the inhibition of post-operative restenosis.

Berk., B. C. et al in the J. Am. Coll. Cardiol. dated 1991 Vol. 17 #6 Supplement B, pp 111B–117B purports to discuss the pharmacologic roles of heparin and glucocorticoids to prevent restenosis after coronary angioplasty.

WO 9209561 (Itoh et al.) purports to teach the use of new ACAT inhibiting amide derivatives in treatment of restenosis after percutaneous transluminal coronary angioplasty.

WO 9208472 (Scarborough et al.) purports to teach the use of platelet antiadhesive peptide(s) obtained from snake venom for the prevention of restenosis following angioplasty.

WO 9207852 (Bovy et al.) purports to teach the use of certain biphenylalkyl xanthine derivatives to prevent post-angioplasty restenosis.

WO 9205782 (Pill, J.) purports to teach the use of thromboxane-A2-receptor antagonists (I) in the preparation of medicaments for inhibition of proliferative developments in obstructive vascular disorders ie. arterial restenosis.

WO 9118639 (GAj et al.) purports to teach the inhibition of stenosis after balloon angioplasty, by the administration of fibronectin by continuous or bolus infusion, or by direct infusion into the stenotic region via the angioplasty catheter.

CA 2,042,159 laid open application (Ondetti, et al.) purports to teach the use of ACE inhibitor (via the oral or parenteral route) for preventing or reducing the risk of restenosis following angioplasty.

U.S. 4,929,602 (Harker, et al.) purports to teach a method of inhibiting arterial restenosis by administration of D-phenyl alanyl-prolyl-arginyl-balomethyl ketone peptide derivative or a hydrolalin acid addition thereof.

U.S. 4,820,732 (Shell, et al.) purports to teach a composition containing a prostaglandin compound for the reduction of restenosis and abrupt stenosis.

Applicant is also aware of a company Glycomed developing a fragment of Heparin that prevents arterial restenosis after balloon angioplasty.

In the basic research efforts in the latter '70s and the early 80's, there existed considerable confusion as to what role immunotherapy should take in cancer. Activation or "hyping" of macrophages was thought to be important. However, in an examination by Romans and Falk of peritoneal macrophages obtained from patients with neoplastic disease, there was definite evidence that these macrophages were already activated yet were co-existing with cancer cells and not causing their destruction.

It has been shown by several independent investigators that the malfunction of macrophages or the putitive block is due to excessive prostaglandin and that this can be altered in tissue culture by corticosteroids, ASA, and the non-steroidal anti-inflammatory drugs, i.e. indomethacin, and naproxen (Naprosyn™). Again, in animal tumors it was repeatedly demonstrated that these substances could alter the response to neoplastic cells and that various combinations of these substances employed with immune enhancing agents could produce very credible success in eliminating experimental tumors. Lala and co-workers combined Indomethacin therapy with Interleukin 2 and showed that this could effect a cure with experiment neoplasm.

There were continued problems with the use of any of these agents in the actual human in vivo experience. All of the non-steroidal anti-inflammatory agents (NSAID) produced major toxicity in terms of gastro-intestinal, neurological, and other areas. Thus, the basis of the present approach is that under general circumstances the use of these agents in human disease, in sufficient amounts, the drug will penetrate to any pathological tissue to alter therapeutically local prostaglandin production. While intravenous preparations exist of Indomethacin and now of other agents, the data is overwhelming, that using these drugs alone produces prohibitive side effects in human subjects. Therefore only insufficient amounts can be brought into the body to effect more than occasional responses in neoplasm.

However the majority of the evidence is present to indicate and therefore it can be postulated that the basis for neoplastic development and how the initial cell "sneaks by" the immune surveillance mechanism relates to its production of prostaglandin. One need postulate only one mutation to alter the amount of prostaglandin synthesis produced by cells when they become "malignant" to establish a mechanism of blocking out the initial cell in any immune reaction, i.e. the macrophage. It therefore became essential to develop a combination of NSAIDS for clinical use to produce a major improvement in response in neoplastic disease and other conditions where excessive prostaglandin synthesis represents the basis of the pathogenesis of this disease state, i.e. arthritis, and various others of the so-called connective tissue inflammatory disorders and/or auto-aggressive diseases.

See also:
1. Modulation of Immunity in Cancer Patients by Prostaglandin Antagonists, *Immunity to Cancer II*, Alan R. Liss, Inc.; and
2. Goodwin, J. S. (1981) Prostaglandin E and Cancer Growth Potential for Immunotherapy with Prostaglandin Synthesis Inhibitors, *Augmentive Agents in Cancer Therapy*, Raven Press, New York.

It is therefore an object of this invention to provide a method of treatment and formulations and pharmaceutical compositions for preventing arterial restenosis after for example balloon angioplasty when endothelial cell proliferation occurs on the inner arterial wall caused by irritation to the cells by balloon angioplasty.

It is a further object of the invention to provide such treatment using hyaluronic acid which is safe and essentially non-toxic.

It is a further object of the invention to provide methods of treatment and formulations and pharmaceutical compositions generally for preventing restenosis and inhibiting restenosis for example post operatively in peripheral vascular systems.

Further and other objects of the invention will be realized by persons skilled in the art from the following summary of the invention and discussion with respect thereto.

SUMMARY OF THE INVENTION

Applicants believe that forms of hyaluronan or hyaluronic acid (especially hyaluronic acid and salts thereof) will prevent stenosis of the inner diameter (ID) of irritated tubular walls and particularly prevent restenosis of the arterial walls by for example the proliferation of endothelial cells as a result of irritation arising from balloon angioplasty or other treatment. The forms of hyaluronic acid (for example hyaluronic acid and salts of hyaluronic acid) can be administered intravenously or by injection (in the case of direct injection of small amounts) in effective amounts of about 10 mg/70 kg person to in excess of 3000 mg/70 kg person prior to, during and/or after injury.

Hyaluronan or hyaluronic acid is a glycosaminoglycan that is evolutionarily conserved and composed of repeating dissacharide units of N-acetyl-glucosamine and glucuronic acid (Laurent and Fraser, 1991, Faseb J., 6:2397). Hyaluronan exerts effects on cell adhesion, motility, growth and differentiation and many of these effects are mediated by the expression of hyaluronan receptors by responding tissues. Thus, hyaluronan was shown to be able to aggregate white cells as a result of its interaction with receptors present on these cells (review, Turley, E. A., 1992, Can, Met. Rev., 11:21). Hyaluronan accumulates almost exclusively at sites of increased receptor expression or in the presence of extracellular hyaluronan binding proteins. Two cell surface associated receptors have been molecularly characterized and include CD44 and RHAMM [Receptor for (Hyaluronan) HA—Mediate Motility]. RHAMM is present in elevated amounts on cells, particularly macrophages and smooth muscle cells responding to injury.

Therefore according to one aspect of the invention, there is provided a process for the prevention of the narrowing of the tubular walls of an animal after the tubular walls have been traumatized (for example wherein the tubular walls are arteries which have been subjected to balloon angioplasty) the process comprising the administration of a therapeutically effective non-toxic amount of hyaluronic acid and/or salts thereof and/or homologues, analogues, derivatives, complexes, esters, fragments and subunits of hyaluronic acid to the animal to prevent narrowing of the tubular walls. (The hyaluronic acid may be administered before, during and/or after the injury). Preferably the form of hyaluronic acid is hyaluronic acid and salts thereof. The amount of the form of hyaluronic acid administered is preferably between about 10 mg/70 kg person and about 3000 mg/70 kg person.

Thus according to another aspect of the invention, a process is provided for the prevention of arterial restenosis after balloon angioplasty in a human, the process comprising the administration of a therapeutically effective non-toxic amount of hyaluronic acid and/or salts thereof and/or homologues, analogues, derivatives, complexes, esters, fragments, and subunits of hyaluronic acid to the human to prevent arterial restenosis. Once again preferably the form of hyaluronan or hyaluronic acid is hyaluronic acid and salts thereof and preferably the amount of the form of hyaluronic acid administered is between about 10 mg/70 kg person and about 3000 mg/70 kg person. The hyaluronic acid can be administered before the procedure, for example, balloon angioplasty or during or after the procedure (immediately following).

The compositions are preferably administered intravenously in a liquid form and include suitable diluents or other adjuvants as required for administration. With respect to the amounts to be administered, they may also be administered by injection preferably at or proximate the site to be treated.

A therapeutically effective amount of stenosis inhibiting drug may be combined with the form of hyaluronic acid for administration. Such drugs may comprise any of those previously mentioned, and those understood by persons skilled in the art. One such drug is heparin. Another is a fragment of heparin.

A therapeutically effective amount of a non-steroidal anti-inflammatory drug (NSAID) for enhancing the effect of the form of hyaluronic acid administered in the prevention of the narrowing of the tubular walls may be administered with the form of the hyaluronic acid. The addition of the non-steroidal anti-inflammatory agent will enhance the activity of the hyaluronic acid in preventing the narrowing of the tubular walls for example enhancing the arterial restenosis prevention effect of the administered hyaluronic acid and/or salts thereof for example by reducing inflammation. The NSAID may be an NSAID suitable for the purposes and may comprise Diclofenac, Indomethacin (solubilized in for example N-Methyl Glucamine), Piroxicam, the (±) tromethamine salt of Ketorolac, acetylsalicylic acid, Naproxen and the like. The amounts of NSAID may be appropriate accepted doses preferably administered to patients. In some cases dose amounts up to 10 mg of the NSAID/kg of body weight (for example 1–2 mg of NSAID/kg of body weight) are suitable. With Diclofenac much larger amounts are appropriate. Where greater than normal amounts of NSAIDS are used, in order to reduce side effects caused by excess NSAID administration, greater than about 200 mg of the form of Hyaluronan or Hyaluronic Acid (HA) per 70 kg person may be administered to reduce and eliminate the side effects such as gastro-intestinal distress, neurological abnormalities, depression, etc., of administration of the NSAID.

A therapeutically effective amount of a free radical scavenger and anti-oxidant such as Vitamin C may also be added to the composition to enhance the effect of the Hyaluronic Acid and Hyaluronan administered. Such amount may be up to 50 grams–100 grams in a dosage as Vitamin C is soluble and is excreted by the kidneys although much lower amounts are normally used. Other anti-oxidants and free radical scavengers may also be used. In one embodiment the composition comprises a form of hyaluronic acid, specifically preferred hyaluronic acid and/or salts thereof, an NSAID, a stenosis inhibiting drug and/or Vitamin C for administration for the prevention of the narrowing of the tubular walls (for example the prevention of arterial restenosis after balloon angioplasty). The composition may comprise a pluality of dosage amounts from which one dosage amount may be withdrawn and used, each dosage amount containing an effective amount of each of the constituents.

Thus according to another aspect of the invention, the use of a pharmaceutical composition for the prevention of the narrowing of the tubular walls of an animal or human after the tubular walls have been traumatized is provided, the use being of a pharmaceutical composition comprising a therapeutically effective non-toxic amount of hyaluronic acid and/or salts thereof and/or homologues, analogues, derivatives, complexes, esters, fragments, and subunits of hyaluronic acid in association with a suitable diluent or pharmaceutically acceptable carrier or other adjuvants to prevent narrowing of the tubular walls—in one embodiment being administered just before the trauma and in another, immediately after the trauma. Preferably the form of hyaluronic acid or hyaluronan is hyaluronic acid and salts thereof, for example sodium hyaluronate.

According to another aspect of the invention, the use of a pharmaceutical composition for the prevention of arterial restenosis after balloon angioplasty in a human is provided, the use being of a pharmaceutical composition comprising a therapeutically effective non-toxic amount of hyaluronic acid and/or salts and/or homologues, analogues, derivatives, complexes, esters, fragments, and subunits of hyaluronic acid in association with a suitable diluent, pharmaceutically acceptable carrier or other adjuvants to prevent arterial restenosis preferably the form of hyaluronic acid is selected from hyaluronic acid and salts thereof and the amount of the form of hyaluronic acid is between about 10 mg/70 kg person and about 3000 mg/70 kg person.

In one embodiment the form of the pharmaceutical composition is for intravenous administration and is administered immediately before the trauma (for example before balloon angioplasty). In another, the composition is administered immediately after the trauma.

According to still another aspect of the invention, the pharmaceutical composition comprises a therapeutically effective amount of non-steroidal anti-inflammatory drug (NSAID) for example Diclofenac, Indomethacin (solubilized in N-Methyl Glucamine), Piroxicam, the (±) tromethamine salt of Ketorolac, acetylsalicylic acid and the like for enhancing the effect of the form of hyaluronic acid in the prevention of the narrowing of the tubular walls.

Thus according to another aspect of the invention, the use of a pharmaceutical composition for the prevention of arterial restenosis after balloon angioplasty is provided, the use being of a pharmaceutical composition comprising a therapeutically effective non-toxic amount of hyaluronic acid and/or salts thereof in association with a suitable diluent or pharmaceutically acceptable carrier or other adjuvants to prevent arterial restenosis (by administration for example intravenously of the composition). In some embodiments the amount of the hyaluronic acid and/or salts thereof is between about 10 mg/70 kg person and about 3000 mg/70 kg person. The composition may further comprise a therapeutically effective amount of a non-steroidal anti-inflammatory drug (NSAID) for enhancing the arterial restenosis prevention effect of the administered hyaluronic acid and/or salts thereof administered. The NSAID may be at accepted appropriate doses depending on the NSAID for example up to about 10 mg/70 kg of body weight (for example 1–2 mg of NSAID/kg of body weight). The appropriate dose for Diclofenac is much greater. Where it is desired to use a dose excess of NSAID, the amount of hyaluronic acid and salts thereof preferably exceeds about 200 mg/70 kg person.

The composition may further comprise a therapeutically effective amount of Vitamin C or other free radical scavanger or anit-oxidant for enhancing the effects of the form of hyaluronic acid to prevent narrowing of the tubular walls. The Vitamin C may be used in large amounts (for example even 50–100 grams) although much smaller amounts are suitable.

The composition may also comprise an effective amount of a stenosis inhibiting drug.

The composition may comprise hyaluronan or hyaluronic acid and at least of one of an NSAID, Vitamin C, free radical scavenger, anti-oxidant and stenosis inhibiting drug.

According to another aspect of the invention the use of:
an effective non-toxic amount of hyaluronic acid and/or salts thereof and/or homologues, analogues, derivatives, complexes, esters, fragments, and subunits of hyaluronic acid,
in the manufacture of a pharmaceutical composition is provided for preventing the narrowing of the tubular walls of an animal after the tubular walls have been traumatized, the use being characterized by a therapeutically effective non-toxic amount of hyaluronic acid and/or salts thereof and/or homologues, analogues, derivatives, complexes, esters, fragments, and subunits of hyaluronic acid being incorporated into the pharmaceutical composition and being sufficient and effective to prevent the narrowing of the tubular walls which were traumatized as for example the arteries being damaged after balloon angioplasty. Preferably the form of hyaluronic acid is hyaluronic acid and/or salts thereof and the composition is in a liquid form. Preferably, the form of hyaluronic acid is utilized at a dose between about 10 mg to about 3000 mg/70 kg person and more preferably the form of hyaluronic acid is utilized at a dose greater than 200 mg/70 kg person. The composition may comprise a plurality of dosage amounts.

In one embodiment the pharmaceutical composition is for prevention of arterial restenosis after balloon angioplasty in humans. In embodiments the pharmaceutical composition is given before the balloon angioplasty and immediately after the trauma.

According to another aspect of the invention, the use of;
(1) hyaluronic acid and/or salts thereof and/or homologues, analogues, derivatives, complexes, esters, fragments, and subunits of hyaluronic acid, and
(2) an agent selected from a non-steroidal anti-inflammatory drug (NSAID), a stenosis inhibiting drug, and Vitamin C, free radical scavenger and anti-oxidant and combinations thereof is provided
in the manufacture of a pharmaceutical composition (including diluents, adjuvants and other carriers) for preventing the narrowing of the tubular walls of an animal after the tubular walls have been traumatized wherein a therapeutically effective amount of the hyaluronic acid and/or salts thereof and/or homologues, analogues, derivatives, complexes, esters, fragments, and subunits of hyaluronic acid is administered to humans together with a therapeutically effective amount of the agent (2), the use being characterized in that the amount of component (1) is an effective amount to prevent the narrowing of the tubular walls of the animal and component (2) enhances the effect of component (1) in the prevention of the narrowing of the tubular walls. Once again the pharmaceutical composition may comprise a plurality of dosage forms from which one dosage amount may be taken.

Preferably component (1) is hyaluronic acid and/or salts thereof and the composition is in a liquid form (for example for intravenous use or injection). Preferably component (1) is utilized at a dose between about 10 mg to about 3000 mg/70 kg person. In one use, component (1) is utilized at a dose greater than 200 mg/70 kg person.

Component 2 is utilized at amounts effective to enhance the effect of Component 1. Vitamin C may be utilized in amounts up to 50–100 grams per dose although much smaller amounts are more desirable. The NSAID can be administered in normally acceptable dose amounts depending on the NSAID. With some NSAIDS the amounts are 1–2 mg of NSAID per Kg of body weight, in others up to about 10 mg per kg bodyweight and in others such as Diclofenac, much larger amounts. Where the NSAID is used in dose excesses (greater amounts than the normally acceptable dose amounts, the amount of the form of hyaluronic acid preferably exceeds about 200 mg per 70 kg person. Suitable NSAIDS include Diclofenac, Piroxicam, Indomethacin (solubilized in N-methyl glucamine), acetylsalicylic acid, ± tromethamine salt of Ketorolac, naproxen and the like.

According to another aspect of the invention a pharmaceutical composition is provided comprising (together with diluents as required) an effective non-toxic amount of hyaluronic acid and/or salts thereof and/or homologues, analogues, derivatives, complexes, esters, fragments, and subunits of hyaluronic acid, for preventing the narrowing of the tubular walls of a human after the tubular walls have been traumatized, the composition being characterized by an effective non-toxic amount of hyaluronic acid and/or salts thereof and/or homologues, analogues, derivatives, complexes, esters, fragments, and subunits of hyaluronic acid being incorporated into the pharmaceutical composition to prevent the narrowing of the tubular walls. Preferably the form of hyaluronic acid is hyaluronic acid and/or salts thereof and preferably the composition is in a liquid form (such as an intraveneous (I.V.) form in an I.V. bag with diluents and pharmaceutically acceptable carriers and adjuvants). The form of hyaluronic acid may be utilized at doses between about 10 mg to about 3000 mg/70 kg person or more and in one embodiment the form of hyaluronic acid is utilized at a dose greater than 200 mg/70 kg person (especially where dosage excesses of NSAIDS are employed). In one embodiment the pharmaceutical composition is for prevention of arterial restenosis after balloon angioplasty in humans. The composition may be administered before the balloon angioplasty and/or after. The pharmaceutical composition may comprise a plurality of dosage amounts from which each dosage amount may be taken.

According to another aspect of the invention, a pharmaceutical composition is provided comprising (together with diluents, adjuvants and other pharmaceutically acceptable carriers as and if desired);
(1) hyaluronic acid and/or salts thereof and/or homologues, analogues, derivatives, complexes, esters, fragments, and subunits of hyaluronic acid, and
(2) an agent selected from a non-steroidal anti-inflammatory drug, a stenosis inhibiting drug, Vitamin C, an anti-oxidant and free radical scavenger and combinations thereof
for preventing the narrowing of the tubular walls of an animal after the tubular walls have been traumatized, the composition being characterized by an effective non-toxic amount of hyaluronic acid and/or salts thereof and/or homologues, analogues, derivatives, complexes, esters, fragments, and subunits of hyaluronic acid being incorporated into the composition together with a therapeutically effective amount of the agent (2), to prevent the tubular walls from narrowing, the composition being characterized that the amount of component (1) is an effective amount to prevent the narrowing of the tubular walls of the animal and the amount of component (2) enhances the effect of component (1) in the prevention of the narrowing of the tubular walls. Preferably component (1) is hyaluronic acid and/or salts thereof most preferably sodium hyaluronate and preferably in a liquid dosage form such as an Intravenous form (I.V. Bag). The composition may be made in bulk and subsequently put into individual dosage amounts. The composition may be packaged such that a plurality of dosage amounts are carried in a container (storage container or reservoir) from which each dosage amount may be withdrawn when needed for use. In some embodiments component (1) may be utilized at a dose between about 10 mg to about 1000 mg/70 kg person. In others the dose amounts may be up to 3000 mg/70 kg person or more. Preferably component (1) is utilized at a dose greater than 200 mg/70 kg person where dose excesses of the NSAID of component (2) are utilized. In one embodiment the pharmaceutical composition is for prevention of arterial restenosis after balloon angioplasty in humans and may be administered before, during and/or after the treatment.

Component 2 is utilized at amounts effective to enhance the effect of Component 1. Vitamin C may be utilized in amounts up to 50–100 grams per dose. The NSAID can be administered in appropriate dose amounts depending on the NSAID and if given in excess amounts the amount of the form of hyaluronic acid preferably exceeds about 200 mg per 70 kg person. Suitable NSAIDS are Diclofenac, Piroxicam, Indomethacin (solubilized in N-methyl glucamine), acetylsalicylic acid, ± tromethamine salt of Ketorolac, naproxen and the like.

When the composition comprises an agent selected from NSAID, stenosis inhibiting drug, Vitamin C, free radical scavenger and anti-oxidant and combinations thereof, Applicants postulate that the hyaluronic acid and/or salts thereof and/or the homologues, analogues, derivatives, complexes, esters, fragments, and/or sub units of hyaluronic acid also facilitates the transport of the agent to the site of irritation to enable the agent to penetrate the cells (in the artery, endothelial cells) which together will help prevent for example arterial restenosis.

By way of example and to illustrate the facilitation of the delivery or transport of a chemical to a site in a mammal, when ethyl alcohol is injected directly into a cancer tumor, and sonographic (ultrasound) assessment is made, it is not dispersed throughout the tumor. When the ethyl alcohol to be administered into a tumor is carried by hyaluronic acid and/or salts thereof, sonographic assessment of the tumor, demonstrates the dispersion of the ethyl alcohol throughout the tumor.

While Applicants postulate that the hyaluronic acid facilitates the transport and delivery, Applicants' invention may be used as described irrespective of the actual method of operation of the hyaluronic acid and/or salts thereof and/or the homologues, analogues, derivatives, complexes, esters, fragments and sub units of hyaluronic acid with the NSAID, stenosis inhibiting drug, Vitamin C, free radical scavenger, and/or anti-oxidant.

The combination of hyaluronic acid and salts thereof and other forms with different chemicals and drugs (for example Vitamin C, NSAIDS, stenosis inhibiting drug, etc.) alters their distribution and performance in the human body and produces an unusual targeting for underperfused tissue and/or pathological tissue. In this regard the use of ascorbic acid (Vitamin C) as a free radical scavenger (50 gm daily–1000 times the daily dose in therapeutic purposes as a Vitamin) administered intravenously with 300–500 mg of hyaluronic acid (sodium hyaluronate) reduces inflammation. The hyaluronic acid enhances the effect of the ascorbic acid. It is thought that this enhanced activity eliminates the free radicals by acting as a free radical scavenger.

A similar situation occurs with the NSAIDS. As a major amount of soluble indomethacin is required, the chemical product was solubilized using n-methyl glucamine at a dilution of 5 mg/ml of n-methyl glucamine (NMG). This substance is then passed through a 22 micron Milipore filter to produce sterility. This material is non-toxic at 16 fold the therapeutic dose in animals and for this reason was considered appropriate to be used in human conditions. Thus, Indocid™ solubilized in NMG is administered to human patients intravenously or intravascularly at a varying dose up to 10 mg/kg where each dose of indomethacin is combined with for example 200–1000 mg of hyaluronic acid (for example "LifeCore™" hyaluronic acid [sodium hyaluronate]) diluted in the original solution of indomethacin and NMG with for example the "LifeCore™" hyaluronic acid. This produces an appropriate mixture and can be administered safely by any of the routes. [Similar clinical studies have been done with hyaluronic acid prepared by other methods, i.e. extraction. The extracted material is satisfactory to use for intravenous.]

Thus when an NSAID for example indomethacin (dissolved in n-methyl glucamine) or other NSAID is administered with greater than 200 mg hyaluronic acid for 1–2 mg/kg body weight of the NSAID (in one instance indomethacin and NMG), no major toxic side effects occur such as gastro-intestinal distress, neurological abnormalities, depression, etc., even at elevated amounts of indomethacin (if necessary). If the amount of hyaluronic acid is decreased below about that amount, the usual side effects may begin to reoccur. In addition, the responses that have been observed are superior when the NSAID (for example Indocid™) is combined with hyaluronic acid demonstrating clearly that the combination is now "targeting" to the tissue when administered by the systemic intravenous route. Thus, it has been observed that patients when receiving in addition to other chemicals (for example ascorbic acid [Vitamin C], 50–200 mg NSAID—hyaluronic acid (sodium hyaluronate) (for example indomethacin and hyaluronic acid) experience dramatic relief of pain immediately. Thus Applicants believe that the addition of the NSAID for example with hyaluronic acid (sodium hyaluronate) prevents enzymatic production of prostaglandin synthetase which blocks macrophage functioning. Thus the hyaluronic acid (and salt and other forms) not only enhance the activity of the NSAID but also reduce any side effects and toxicity that is associated with the use of the prostaglandin synthesis inhibitors.

The hyaluronic acid and salts thereof may be utilized at varying doses—10 to 1000 mg/70 kg person. As there is no toxicity, the hyaluronic acid can obviously be administered in a dose excess (for example 3000 mg/70 kg individual) without any adverse effects.

One form of hyaluronic acid and/or salts thereof (for example sodium salt) and homologues, analogues, derivatives, complexes, esters, fragments, and sub units of hyaluronic acid, preferably hyaluronic acid and salts and thereof suitable for use with Applicant's invention is a fraction supplied by Hyal Pharmaceutical Corporation. One such fraction is a 15 ml vial of Sodium hyaluronate 20 mg/ml (300 mg/vial—Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) and homologues, analogues, derivatives, complexes, esters, fragments, and/or sub units of hyaluronic acid, preferably hyaluronic acid and salts thereof may comprise hyaluronic acid and/or salts thereof having the following characteristics:

a purified, substantially pyrogen-free fraction of hyaluronic acid obtained from a natural source having at least one characteristic selected from the group consisting of the following:
      i) a molecular weight within the range of 150,000–225,000;
      ii) less than about 1.25% sulphated mucopolysaccharides on a total weight basis;
      iii) less than about 0.6% protein on a total weight basis;
      iv) less than about 150 ppm iron on a total weight basis;
      v) less than about 15 ppm lead on a total weight basis;

vi) less than 0.0025% glucosamine;
vii) less than 0.025% glucuronic acid;
viii) less than 0.025% N-acetylglucosamine;
ix) less than 0.0025% amino acids;
x) a UV extinction coefficient at 257 nm of less than about 0.275;
xi) a UV extinction coefficient at 280 nm of less than about 0.25; and
xii) a pH within the range of 7.3–7.9. Preferably the hyaluronic acid is mixed with water and the fraction of hyaluronic acid fraction has a mean average molecular weight within the range of 150,000–225,000. More preferably the fraction of hyaluronic acid comprises at least one characteristic selected from the group consisting of the following characteristics:
i) less than about 1% sulphated mucopolysaccharides on a total weight basis;
ii) less than about 0.4% protein on a total weight basis;
iii) less than about 100 ppm iron on a total weight basis;
iv) less than about 10 ppm lead on a total weight basis;
v) less than 0.00166% glucosamine;
vi) less than 0.0166% glucuronic acid;
vii) less than 0.0166% N-acetylglucosamine;
viii) less than 0.00166% amino acids;
x) a UV extinction coefficient at 257 nm of less than about 0.23;
xi) a UV extinction coefficient at 280 nm of less than 0.19; and
xii) a pH within the range of 7.5–7.7.

Other forms of hyaluronic acid and/or its salts, and homologues, derivatives, complexes, esters, fragments and sub units of hyaluronic acid may be chosen from other suppliers. Applicants propose the use of sodium hyaluronate produced and supplied by LifeCore ™ Biomedical, Inc. having the following specifications.

| Characteristics | Specification |
|---|---|
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |

| Heavy Metals, maximum ppm | | | | | | | | |
|---|---|---|---|---|---|---|---|---|
| As | Cd | Cr | Co | Cu | Fe | Pb | Hg | Ni |
| 2.0 | 5.0 | 5.0 | 10.0 | 10.0 | 25.0 | 10.0 | 10.0 | 5.0 |

| | |
|---|---|
| Microbial Bioburden | None observed |
| Endotoxin | <0.07 EU/mg NaHy |
| Biological Safety Testing | Passes Rabbit Ocular Toxicity Test |

Applicants also propose the use of forms of hyaluronic acid described in the prior art.

The following references teach hyaluronic acid, sources thereof and processes of the manufacture and recovery thereof.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 $cm^3/g.$, and preferably greater than about 2000 $cm^3/g.$;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11 \times 10^3$ degree—$cm^2$/mole (of disaccharide) measured at 220 nanometers;

(f) no significant cellular infiltration of the vitreous and anterior chamber, no flare in the aqueous humor, no haze or flare in the vitreous and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

Where high molecular weight hyaluronic acid (or salts or other forms thereof) is used, it must be diluted to permit administration and ensure no coagulation or interference with body function.

One formulation of Ascorbic Acid (Vitamin C) injection USP is manufactured by Steris Laboratories, Inc., Phoenix, Ariz., 85043 U.S.A. and comprises 22 mg/ml (equivalent to sodium ascorbate 250 mg/ml) in 30 ml, 50 ml, or 100 ml individual containers, 30 ml size being preferred.

BRIEF DESCRIPTION OF THE DRAWINGS

Surgical procedures were undertaken to illustrate an embodiment of the invention and analysis of results are illustrated in the enclosed Figures in which;

FIGS. 7, 8, 9, 10, 11 and 12 relate to the article entitled "Neointimal Formation after Balloon Catheter Injury: A Role of Hyaluronan and the Hyaluronan Receptor RHAMM" whose contents are reproduced from page 22, line 24 to page 36, line 31, of this Disclosure.

FIG. 7 are photographs of endothelial and smooth muscle cells of cartoid arteries of the scarified rats used in the test.

FIG. 8 illustrates the expression of various isoforms of RHAMM after specified times.

FIG. 9 illustrates the Distribution of Hyaluronan.

FIG. 10 illustrate "THE EFFECT OF RHAMM HA-BINDING PEPTIDE (410–411) ON THE CHEMOTAXIS OF NEUTROPHILS TO IL-8".

FIG. 11 illustrates "THE EFFECT OF RHAMM HA-BINDING PEPTIDE (401–411) AND ANTI-RHAMM ANTIBODY ON THE CHEMOTAXIS OF MACROPHAGE CELL LINES TO COMPLEMENT (C5a)".

FIG. 12 illustrates "EFFECT OF RHAMM HA-BINDING PEPTIDE 401–411 ON SMOOTH MUSCLE CELL MIGRATION 5 HOURS AFTER WOUNDING".

BRIEF DESCRIPTION OF THE PREFERRED EMBODIMENTS

The following experiments were conducted.

10 rabbits were anesthetized and balloon angioplasty was performed on them. The rabbits were perfused with hyaluronan (5 mg/ml) or buffer alone and allowed their recover. Rabbits were sacrificed at 2, 24, 48 hours after injury and carotid arteries were processed for histology and serial 5–10 $\mu$m sections were taken for processing. Sections were stained with hematoxylin or with anti RHAMM antibodies. 10 sections of each treatment were analyzed.

The results of the analysis is described below with respect to the Figures.

Figure 1:
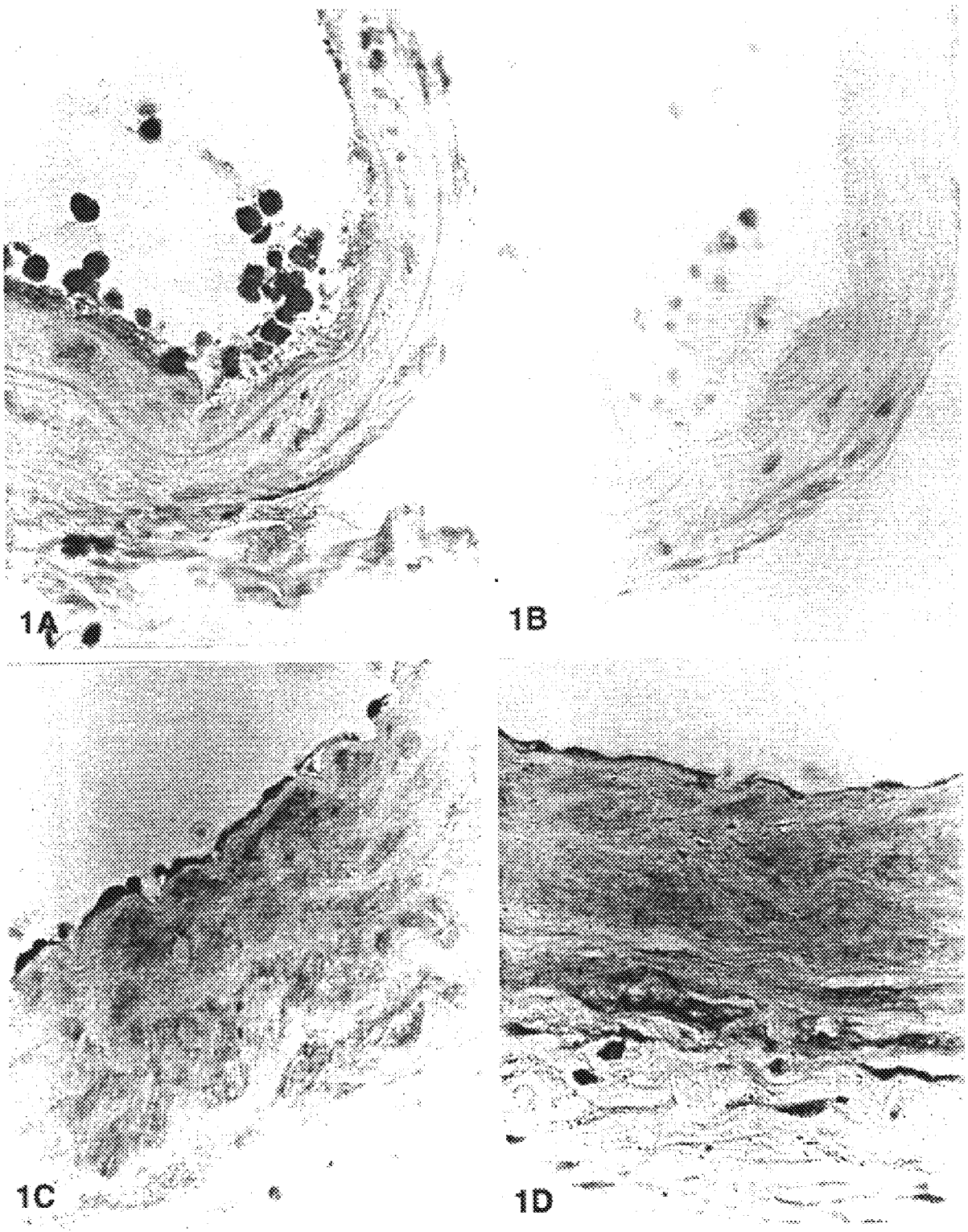
FIG. 1 contains photographs of injured and sham operated arteries.

FIG. 1: Injured carotid arteries show denudating of the endothelia cell layer and adherence of white cells (FIG. 1A). White cells stained positively for RHAMM relative to IgG control background (FIG. 1B). Carotid arteries that were exposed to hyaluronan (FIG. 1C) or sham operated arteries (FIG. 1D) show intact endothelial cell layer and do not exhibit accumulations of white cells.

Figure 2:
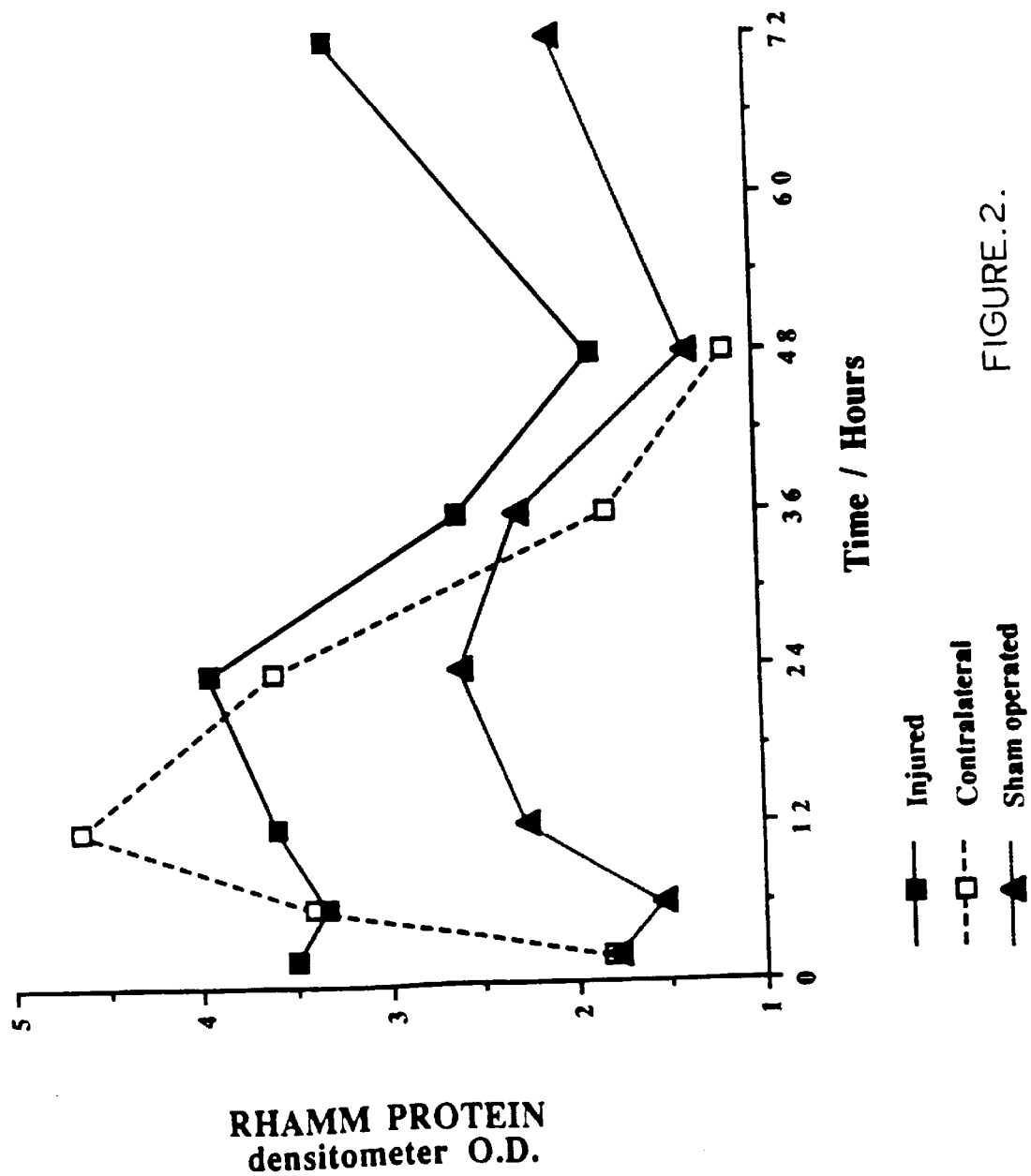
FIG. 2 illustrates in graph form RHAMM (Receptor for HA (Hyaluronan) Mediated Motility) expression by the carotid arteries.

FIG. 2: Western transblot analysis of RHAMM expression by carotid arteries. Carotid arteries were homogenized, the released proteins were electrophoresed on SDS-PAGE and the presence of RHAMM was detected with a mono-specific antibody. The presence of the antibody was visualized with chemiluminescence and the relative amounts of bound antibody were quantified with optical densitometry. Operated animals displayed an acute, large rapid increase in the presence of RHAMM. Levels of RHAMM had dropped by 5–6 days after tissue injury. Sham operated animals showed no increase in RHAMM expression.

Figure 3:
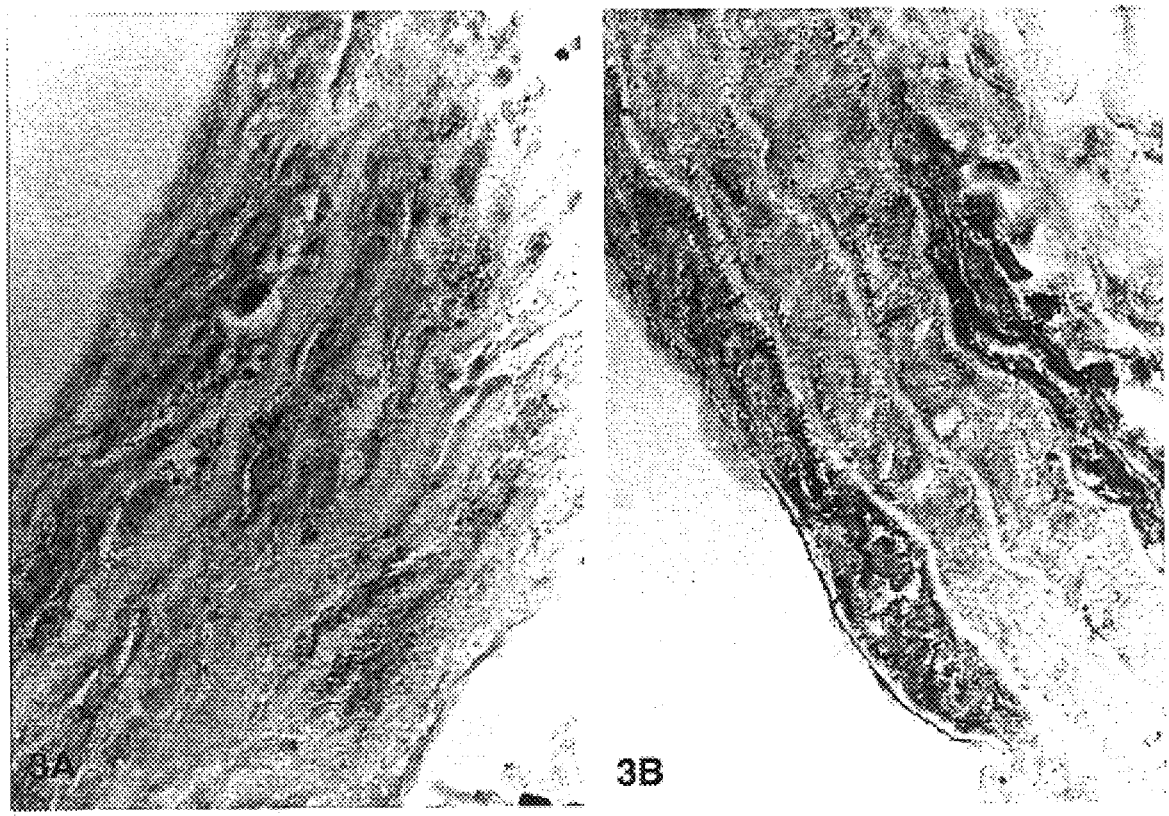
FIG. 3 contains photographs of RHAMM and hyaluronan expression in smooth muscle cells of the carotid artery 4 days after their injury.
Figure 3:
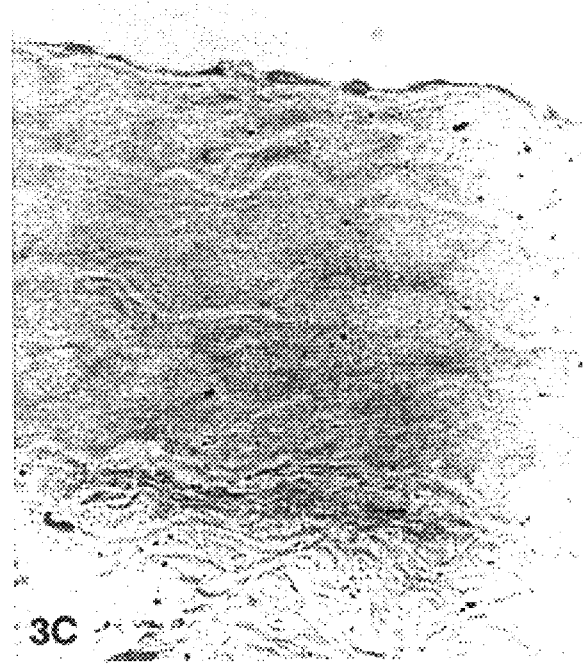

FIG. 3: RHAMM (FIG. 3A) and hyaluronan (FIG. 3B) expression in smooth muscle cells of the carotid artery 4 days after their injury. RHAMM expression on white cells elevated immediately (FIG. 1) while RHAMM expression on smooth muscle cells was increased later and concommittent with the initiation of their locomotion. Smooth muscle cells of sham operated animals did not show a similar increase in the expression of RHAMM (FIG. 3C).

Figure 4:
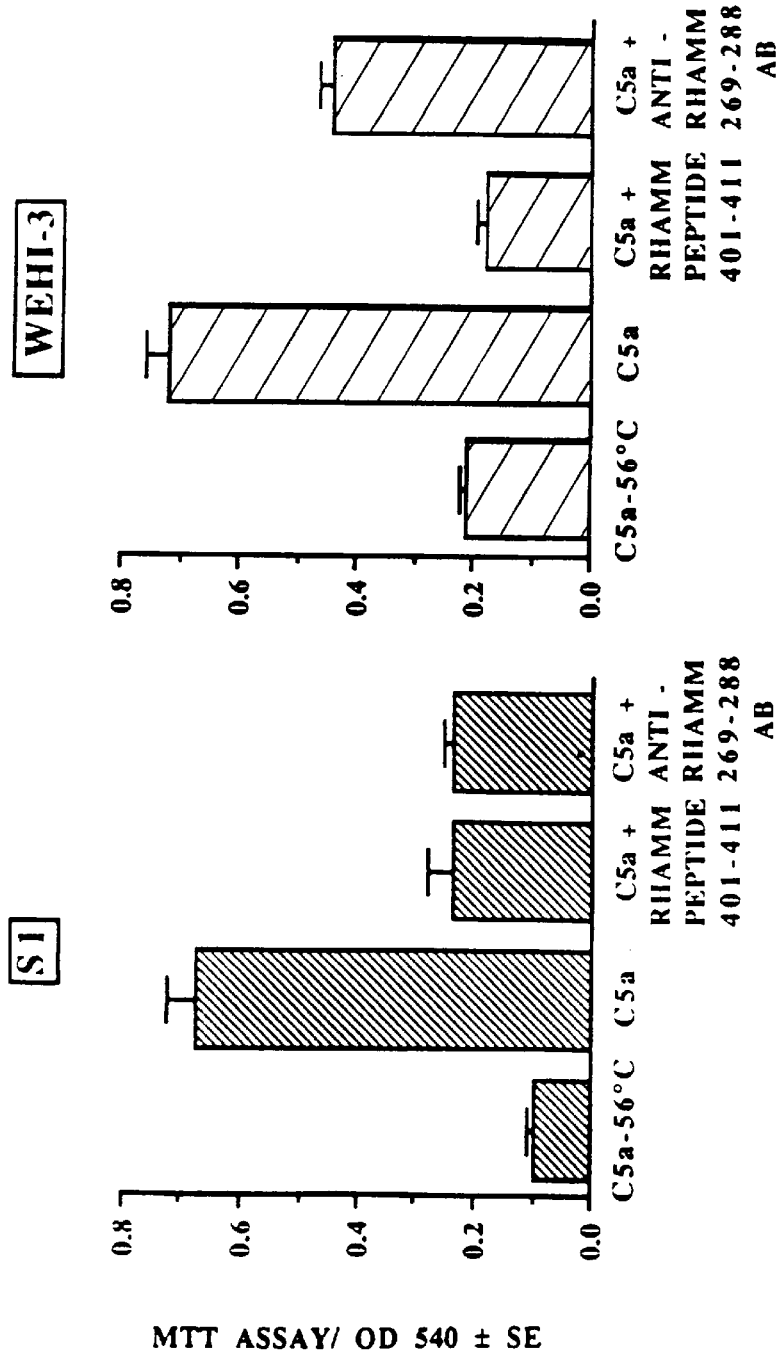
FIG. 4 illustrates in a bar graph the effect of RHAMM, HA binding [Hyaluronan-(Hyaluronic Acid)-binding] peptides (401–411) and anti-Rhamm antibody on the Chemotaxis of Macrophage cell lines to complement (C5a).

FIG. 4: The effect of RHAMM peptides on chemotaxis of neutrophiles in response to IL-8. RHAMM peptides that mimic the hyaluronan binding domain of RHAMM inhibit the chemotaxis of neutrophiles in a Boyden chamber assay.

Figure 5:
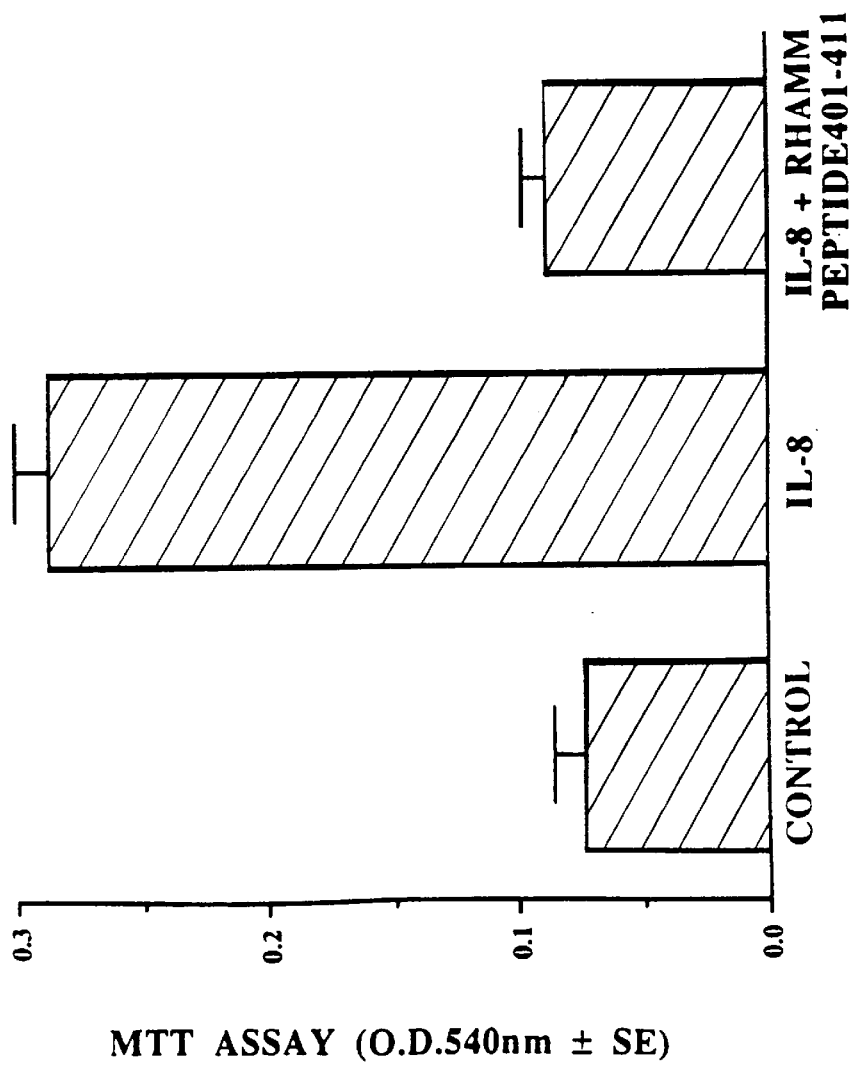
FIG. 5 illustrates in bar graph form the effect of RHAMM HA-Binding peptides (401–411) of the chemotaxis of the neutrophiles to IL-8.

FIG. 5: RHAMM peptides and antibodies inhibit chemotaxis of macrophage cells lines (S1, WEHI-3) in response to complement. Complement but not heat-inactivated complement (56° C.) stimulated chemotaxis of macrophage cell lines. RHAMM peptides that mimic hyaluronan binding domain of RHAMM and anti-RHAMM antibodies inhibit chemotaxis.

Figure 6:
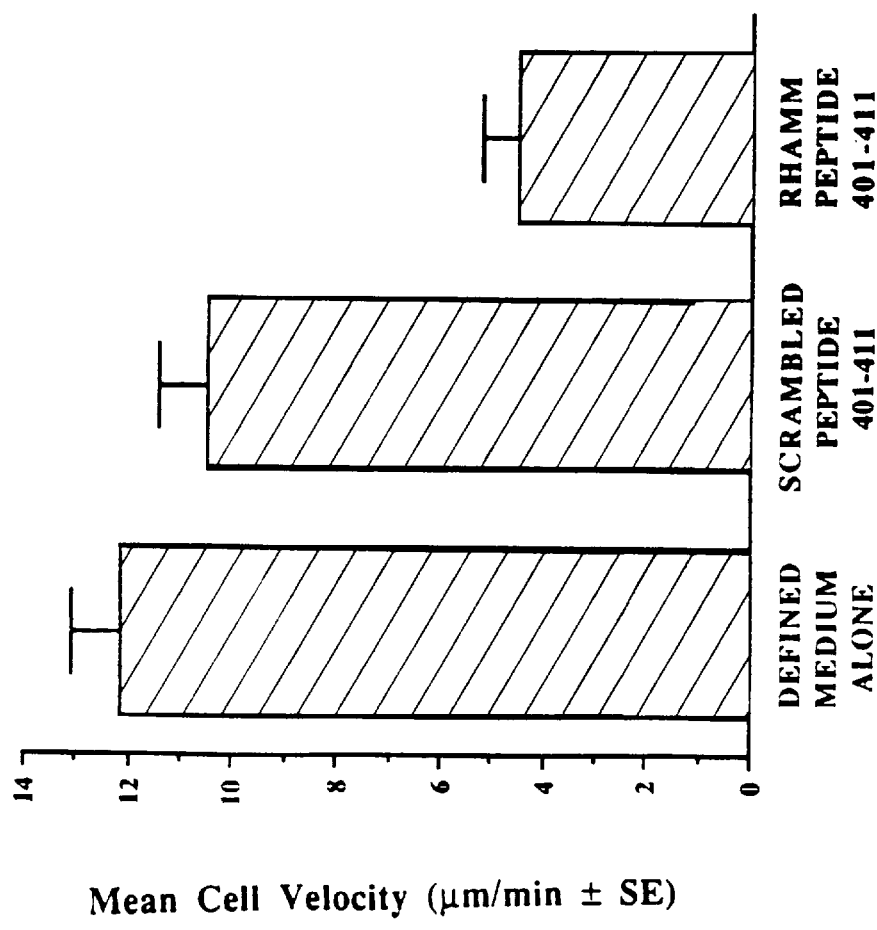
FIG. 6 illustrates in bar graph form the effect of RHAMM HA-binding peptide 401–411 on smooth muscle cell migration 5 hours after wounding.

FIG. 6: RHAMM peptides inhibit the locomotion of smooth muscle cells responding to injury. The RHAMM peptide that mimics the hyaluronan binding domain of RHAMM inhibits the locomotion of injury smooth muscle cells. The scrambled peptide had no effect indicating the specificity to the "sense" peptide.

RHAMM expression (determined by a method of detection named Western transblot analysis using mono-specific antibodies to RHAMM (Turley, e. A., Austin, L., Vandeligt, K. and Clary, C., 1991, J. Cell Biol., 112:1041), revealed an acute increase in expression of this receptor that was detectable by two hours (FIG. 2), a time frame during which white cells were observed in control animals to adhere to the endothelium (FIG. 2). [For a further discussion of RHAMM see the article "Identification of Two Hyaluronan-binding Domains in the Hyaluronan Receptor RHAMM", Baihua Yang, Liying Zhang, and Eva Ann Turley, The Journal of Biological Chemistry, Vol. 268, No. 12, Issue of April 25, pp. 8617–8623, 1993.] RHAMM was also increased in the contralateral artery suggesting the release of a soluble factor that regulates RHAMM expression from the injured tissue. However, sham operated animals showed little increase in the expression of RHAMM (FIG. 2). In experimental animals, expression of RHAMM was maintained for several days, then levels dropped. Examination of fixed tissue revealed that the major cells expressing RHAMM were activated white cells and smooth muscle cells (FIG. 1, 3). The involvement of RHAMM in white cell and smooth muscle cell locomotion was assessed in vitro using image analysis to measure random locomotion and Boyden chambers to measure chemotaxis. Peptides (100 ng/plate) that mimic regions (in particular the hyaluronan binding domains) of RHAMM, inhibit macrophage (FIG. 4) neutrophiles (FIG. 5) and smooth muscle cell (FIG. 6) migration to a highly significant degree (p>0.0001, Student's "T" test). Collectively, these results indicate that RHAMM, and in particular its Hyaluronan binding capability, is essential for locomotion of white cells and smooth muscle cells and that its expression is elevated at the site of tissue injury following experimental ballon catherization in rabbits.

Hyaluronan treatment of rabbits just prior to their injury abolished adherence of white cells to endothelium resulting in tissue that appeared intact as detected by histological criteria (FIG. 1). Several days after injury, carotid arteries of hyaluronan treated rabbits appeared similar to controls displaying an intact endothelium.

The rationale for these results is that hyaluronan bound to cells expressing high levels of its receptor, RHAMM and prevented subsequent interactions of these cells with the endothelium. It is expected, that expression of the other hyaluronan receptor, CD44, is also elevated.

For a discussion and illustration of terms and expressions in this application, reference should be had to the unpublished article entitled "Neointimal Formation after Balloon Catheter Injury: A Role of Hyaluronan and the Hyaluronan Receptor RHAMM", which is reproduced hereinafter, the portions thereof which discuss and illustrate terms and expressions referred to previously being incorporated into the disclosure of the invention herein before written.

"Neointimal Formation after Balloon Catheter Injury: A Role of Hyaluronan and the Hyaluronan Receptor RHAMM".

Abstract

Since hyaluronan (HA) and its interaction with the HA receptor RHAMM (Receptor for HA-Mediated Motility) have been implicated in smooth muscle cell migration in vitro, we investigated the expression of these molecules in an in vitro model of injury that affects smooth muscle cells, the balloon catheter de-endothelialization of the rat carotid artery. Leukocytes and smooth muscle cells were primarily affected in the expression of RHAMM following injury. Two hours after injury, neutrophils and macrophages had adhered to the site of injury and strongly expressed RHAMM. By six hours, a subpopulation of medial smooth muscle cells that demonstrated increased expression of RHAMM could be identified next to the internal elastic lamina. Forty eight hours after de-endothelializtion, a layer of smooth muscle cells, staining strongly for both RHAMM and HA, had formed adjacent to the lumen. From 7 to 14 days after injury, this neointimal layer continued to express high levels of RHAMM, but HA expression was restricted to cells at the junction of the medial and neointimal layers. Two isoforms of RHAMM (65 and 84 kDa) were noted in control arteries. Coincident with the increased staining for RHAMM and HA observed in injured arteries, a 70 kDa isoform, that may represent a membrane form of RHAMM, appeared between 36 and 72 hours after injury. Macrophage and neutrophil chemotaxis was inhibited by anti-RHAMM antisera and by a peptide encoding a RHAMM HA-binding domain. Smooth muscle cell migration following in vitro wounding was also inhibited by these reagents. Collectively, these results suggest that HA and RHAMM play a role in migratory responses to vascular injury.

Introduction

Balloon catheter-induced de-endothelialization of the rat carotid artery is a well-established model of restenosis after balloon angioplasty[1]. A sequence of inflammatory cell adherence, smooth muscle cell proliferation and migration into the intima, followed by excess extracellular matrix production result in stenosis of the affected vessel after injury to the endotheliuml-[15]. Growth factors such as platelet-derived growth factor (PDGF)[6] and transforming growth factor β(TGF-β)[7], hormones such as angiotensin[8], and proteases such as tissue—and urokinase-plasminogen activators[9] regulate this process. Inflammatory cells may also modulate the responses by producing a wide array of growth factors including PDGF and TGF-$β_1$. Upon injury, a small proportion of the smooth muscle cells within the medial layer undergo proliferation, and the neointimal layer is formed by the migration of these cells through the internal elastic lamina[11]. Excess extracellular matrix deposition by these smooth muscle cells leads to a reduction in the size of the lumen of the injured artery[12]. The mechanism(s) by which inflammatory cell chemotaxis and smooth muscle cell migration occur following in vivo injury remain unclear.

We have previously shown in vitro that the RHAMM:HA interaction is necessary for the migration of ras-transformed cells[13] and smooth muscle cells into wounds (Savani et al., submitted). Injury to the monolayer resulted in an increase in cell-associated HA, expression of a novel 70 kDa isoform of RHAMM, and cell surface localization of RHAMM concomitant with high rates of locomotion after injury. Further, polyclonal RHAMM antisera that block HA binding to this receptor inhibited the migratory response to wounding (Savani et al., submitted). In this study, we investigated the distribution and expression of both RHAMM and HA in balloon-catheter injured rat carotid arteries during the development of the neointima, and studied the effects of anti-RHAMM antisera and RHAMM peptides on chemotaxis and migration of vascular cells.

Materials and Methods

Animals

Male Sprague-Dawley rates (Charles River) weighing 325–350 g and aged 15 weeks were used throughout these experiments.

Balloon Catheter Injury

Animals were anesthetized with 80 mg/kg of ketamine (Aveco) and 6 mg/kg xylazine (Haver) intramuscularly. The left carotid artery was exposed and a 2F Fogarty balloon catheter (Baxter, model 12-060–2f) was introduced into the lumen. With the balloon inflated, the catheter was passed through the common carotid three times to remove the endothelium. Both common carotid arteries from injured animals were harvested. Sham operated animals had their left carotid artery exposed without passage of the catheter and the right artery was harvested for study.

Anti-RHAMM Antiserum and RHAMM HA-binding Peptide

A polyclonal antiserum (Anti-peptide $aa^{269-288}$ Ab, Savani et al., submitted) was raised in rabbits to a peptide ($aa^{269-288}$) encoded in the RHAMM cDNA[14]. This antiserum has been shown to block both HA-stimulated random locomotion and migration of smooth muscle cells following wounding. Further, it partially blocks HA-binding to RHAMM (Savani et al., submitted).

The HA-binding region of RHAMM consists of two 10 amino acid domains located close to the carboxy terminus of the protein[15]. A peptide mimicking Domain I (amino acides$^{401-411}$)—YKQKIKHVVKLK— and a scrambled peptide consisting of the same amino acids arranged in a random manner —RQKVLKRQLKS— were synthesized at the Manitoba Institute of Cell Biology. Both peptides were used at a final concentration of 2 μg/mL in locomotion assays.

Immunocytochemistry

Arteries harvested for immunocytochemistry were fixed in 10% phosphate buffered formalin, embedded in paraffin and processed to obtain 5 μm sections. Non-specific sites on the tissue were blocked with 1.5% goat serum in 0.01 M Tris buffered saline (TBS) for 1 hour. The sections were incubated overnight either with Anti-peptide $aa^{269-288}$ Ab (1:100 dilution) dissolved in 0.01M TBS with 1.5% goat serum to detect RHAMM, or with the biotinylated HA binding region of aggrecan (1:300 dilution) isolated from bovine nasal cartilage[16] to detect HA. The sections for RHAMM staining were incubated with biotinylated goat anti-rabbit IgG (Vectastain ABC peroxidase kit, Vector Laboratories, Burlingame, Calif. 5 μL/mL of 0.01M TBS). The activity of endogenous peroxidases was quenched with 0.6% hydrogen peroxide in methanol (Mallinckrodt) for half an hour at room temperature (RT). All sections were then incubated with an avidin-biotin-peroxidase complex (Vectastain, Vecto Labs.) for 1 hour at RT. Staining was obtained using diaminobenzadine (DAB, Sigma, 10 mg/mL in 0.05M TBS) and the reaction was stopped with distilled water. The color of the reaction product was enhanced with 0.5% copper sulfate in 0.9% NaCl for 10 minutes. Sections were counterstained using 0.25% methyl green for 15 minutes. After clearing in n-butanol and xylene, the sections were mounted in Permount® (Fisher Scientific). The specificity of staining for RHAMM was confirmed by the greatly reduced staining observed following the use of serum from which RHAMM antibodies had been removed by affinity chromatography.

Specifically of staining for HA was confirmed both by incubation of the probe with excess HA prior to staining, and by pretreatment of the sections with Streptomyces hyaluronidase to degrade HA prior to staining. Normal rabbit IgG (5 μg/mL, Sigma) and anti-cytoskeletal actin antibody (1:1000 dilution, Sigma) were used as negative and positive controls respectively.

Immunoblots

Carotid arteries were snap frozen in liquid nitrogen and maintained at −80° C. until further analysis. The tissue was homogenized in lysis buffer [25 mM Tris HCl, 0.1% sodium dodecyl sulfate, 1% triton X-100, 1% sodium deoxycholate, 0.15 M NaCl, 1 mM EDTA, and the protease inhibitors leupeptin (1 μg/mL), phenylmethyl sulfonylfluoride (2 mM), pepstatin A (1 μg/mL), aprotinin (0.2 TIU/mL) and 3,4-dichloroisocoumarin (200 μM)]. Protein concentration was determined by the DC protein assay method (BioRad, Richmond, Calif.) using an equal sample of the lysis buffer for background determination. Five μg of protein from each sample was separated on 10% SDS-PAGE, transblotted onto nitrocellulose membranes. Additional protein binding sites were blocked with 5% defatted milk in TTBS (0.01 M Tris base, 150 mM NaCl, pH 7.4, with 0.0.5% Tween 20, Sigma Chemical Co., St. Louis, Mo.). Blots were incubated with the primary antibody (Anti-peptide $aa^{269-288}$ Ab, 1:250 dilution in 1% defatted milk in TTBS) overnight at 4° C. The primary antibody was detected using goat anti-rabbit IgG antibody conjugated to horse radish peroxidase (Sigma Chemical Co., St. Louis, Mo.; 0.2 μg/mL in 1% defatted milk in TTBS) incubated for one hour at room temperature and was visualized with chemiluminescence (ECL, Amersham) as per manufacture's instructions.

Cells and Cell Lines

Smooth muscles cells were isolated from bovine aorta as described previously for rate aorta[17] and were maintained in Dulbecco's Modified Eagles medium (DME) supplemented with 10% fetal calf serum (FCS) and 20 mM Hepes buffer, pH 7.2 at 37° C. and 5% $CO_2$ in air. All experiments were performed using defined medium [DM, Dulbecco's Modified Eagles medium with 20 mM HEPES buffer, pH 7.2, 0.5 U/mL insulin (beef and pork zinc suspension, Novo Laboratories Ltd., Willowdale, Ontario) and 4 μg/mL transferrin (Sigma Chemical Co., St. Louis, Mo.)], and the culture medium was replaced 24 hours before filming. Wounding injury to confluent monolayers consisted of removal of half the monolayer using a cell lifter followed by the addition of fresh DM in the presence of either RHAMM peptide $aa^{401-411}$ or the scrambled peptide of the same domain as described above.

The macrophage cell lines S1 and WEHI-3 were used to analyze the effect of antibodies and synthetic peptide on macrophage chemotaxis to endotoxin-activated mouse serum (AS). These cell lines were also maintained in DME with 10% FCS and 20 mM Hepes buffer, pH 7.2 at 37° C. and 5% $CO_2$ in air.

Human neutrophils were obtained from peripheral blood samples of normal volunteers and mixed in ACD solution (0.085) M trisodium citrate, 0.065 M citric acid, 2% Dextrose) to prevent clotting. 5% Dextran was added and the separated plasma and white blood cells were removed. The cells were washed twice in PBS, pH 7.2 and a Ficoll gradient was used to separate the lymphocytes. The isolated neutrophils were then washed and resuspended in PBS. Red cells were lysed by brief exposure to hypotonic PBS.

Timelapse Cinemicrography

Injured cell monlayers were monitored for motility using an IM 35 Zeiss inverted microscope to which a video camera (Hamamatsu CCD, Inc., Japan) was attached. The cells were maintained at 37° C. using a heated plaform (TRZ 3700, Zeiss, Germany). Cell locomotion was followed by using image analysis (Image 1, Universal Imaging Corp., Westchester, Pa.). This program allows quantification of nuclear displacement from a sequence of digitalized images. The motility of thirty cells in each experiment was followed for a period of 24 hours with mean velocities calculated every hour.

Chemotaxis Assay

Chemotaxis was stimulated using either bacterial endotoxin-activated mouse serum (AS), prepared according to Stevenson et al.[18] for macrophage cell lines, or 100 ng/mL interleukin-8 (IL-8) for meutrophils. Heat-inactivated serum (56° C. for 20 minutes) or medium served as negative controls respectively. The chemotactic assay developed in our colormetric assay developed in our laboratory and described in detail elsewhere[19]. Briefly, a 96-well chemotaxis chamber with a lower recess large enough to hold a microtiter plate (Neuro Probe, stock# MBA96) and a 5 μm framed filter (Neuro Probe, used PED5/A) were used. The microtiter plate was filled with chemoattractants and controls and placed in the recess of the chemotaxis chamber. The framed filter was then placed on the top of the filled microtiter plate. The chamber was then closed and 200 μl of a cell suspension ($2.5 \times 10^5$ cells/mL) in DME was then added to the wells of the upper plate. The chamber was incubated at 37° C. for 4 to 6 hours in 5% $CO_2$ in air. After incubation, the medium in the wells of the upper plate was replaced with 200 μl of PBS containing 20 μM EDTA and incubated at 4° C. for 30 minutes. Cells remaining on the top of the polycarbonate membrane were removed with cotton Q-tips. The cells which had migrated into or through the filter were collected by centrifugation with a 50 ml tube adaptor at 500 g for 10 minutes and transfered into a 96-well plate. The number of displaced cells was quantified by the addition of 3-(4.5-dimethylthiazol-2-yl)-2.5-diphenol tetrazolium bromide (MTT) to a final concentration of 250 μg/mL that was incubated at 37° C. for 4 hours. The dark purple crystals produced by the reduction of MTT were dissolved by mixing with 100 μl of acid-isopropanol (2 mM HCl). The plate was analyzed within 2 hours on a microtiter plate ELISA reader with a filter of 540 nm. The degree of MTT reduction corresponds to relative cell number[19].

Results

RHAMM and HA expression increases following balloon catheter injury of the carotid artery.

The endothelial and smooth muscle cells of carotid arteries obtained from uninjured rats was weakly positive for RHAMM (FIG. 7A). Two hours after injury, neutrophils and macrophages adhered to the denuded area and strongly expressed RHAMM (FIG. 7B). However, by six hours after injury, a proportion of smooth muscle cells showed increased expression of RHAMM (FIG. 7C), and by 48 hours, smooth muscle cells that formed the neointima stained stained strongly for RHAMM (FIG. 1d). By 7 days, and up to 14 days after injury, there was an increase in the size of the neointimal layer. Cells in this layer continued to express high levels of RHAMM (FIGS. 7E & 7F). Sections incubated with preimmune IgG or anti-RHAMM antisera that had been chromatographed on a RHAMM-GST fusion protein column to remove anti-RHAMM antibodies showed no staining (data not shown).

Figure 7:
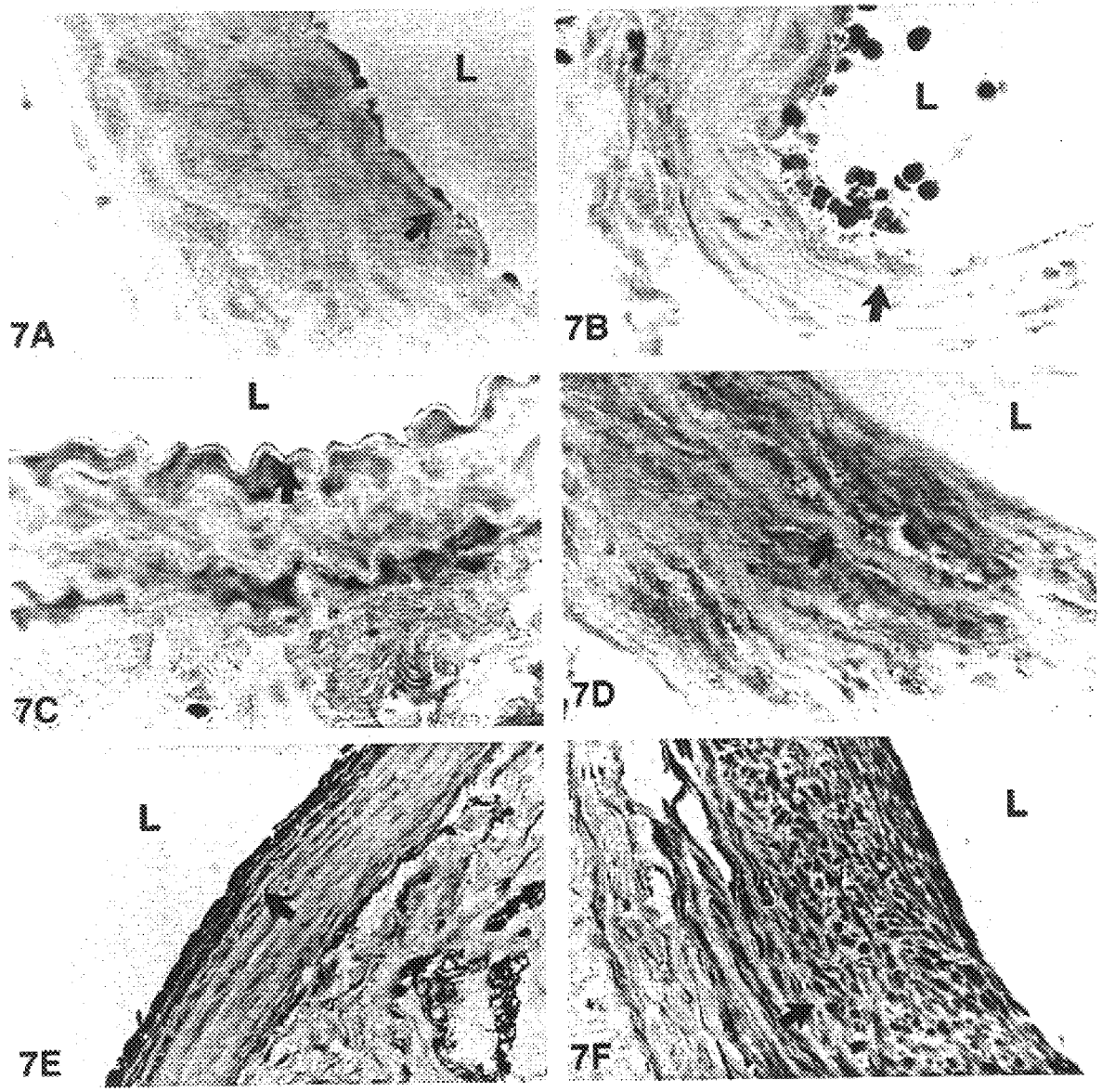
Figure 8:
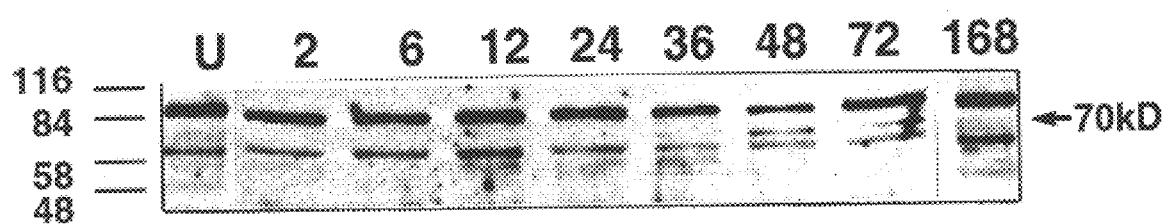

The expression of RHAMM was further investigated using western blot analysis of arteries from injured and sham operated animals using Anit-peptide $aa^{269-288}$ Ab. In uninjured arteries, constitutive expression of two isoforms of RHAMM of mw 84 and 65 kDa was observed (data not shown). However, in injured arteries, a consistently elevated expression of the 84 kDa isoform of RHAMM was observed between 2 and 24 hours after de-endothelialization (FIG. 8) after which expression of this isoform decreased (FIG. 8). A subssequent increase in the 84 kDa isoform was noted from 72 hours and continued up to 168 hours (FIG. 8). There were only minimal changes in the expression of the 65 kDa isoform in injured arteries (FIG. 8). Interestingly, an additional isoform of mw 70 kDa was expressed from 36 to 72 hours after injury (FIG. 8), coinciding temporally with the strong staining for RHAMM and HA observed in injured arteries (FIG. 7).

Figure 9:
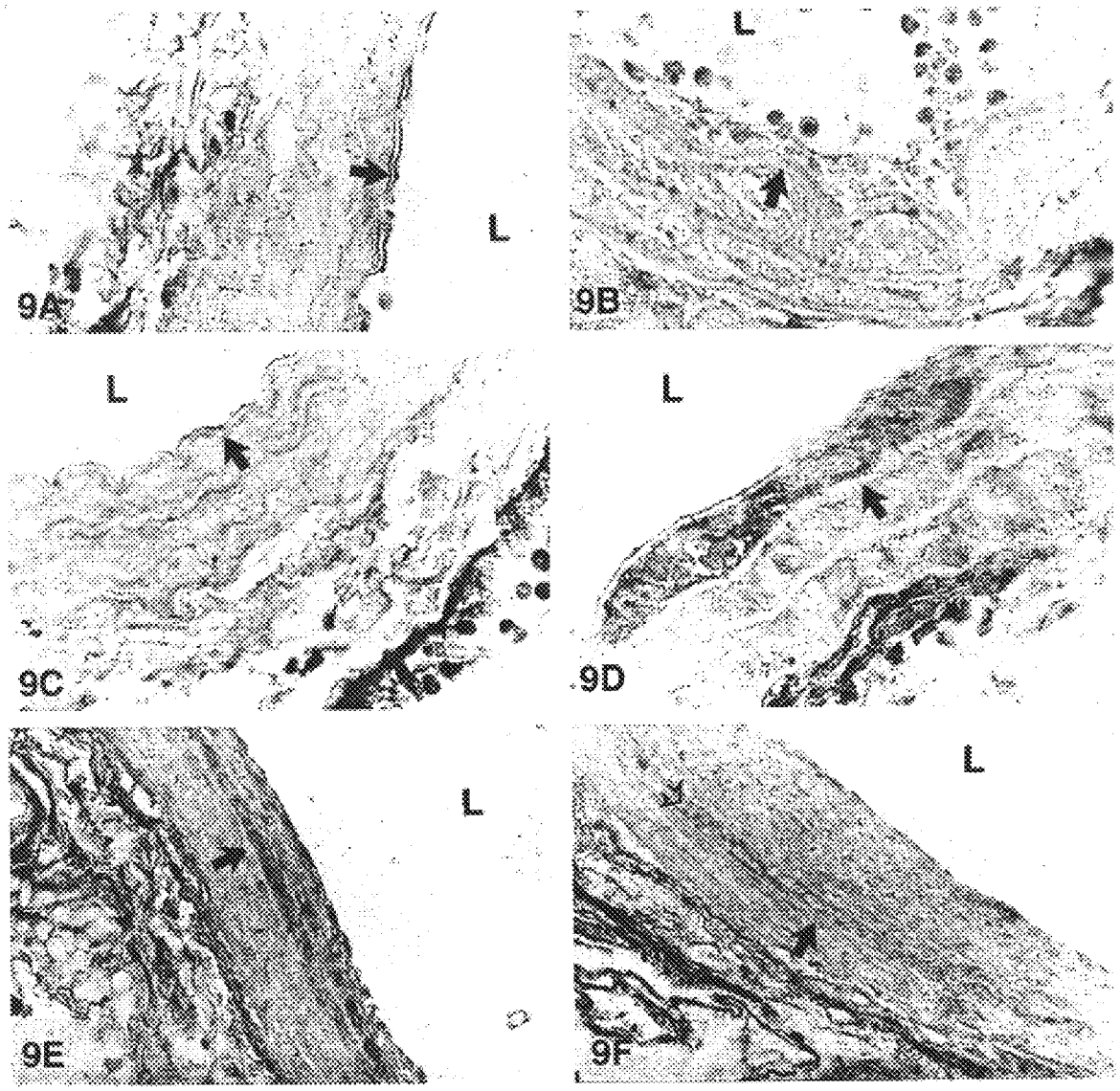

Distribution of HA in the uninjured carotid was restricted to the endothelium and the adventitia (FIG. 9A). Two hours after injury, the neutrophils and macrophages adherent to the denuded area showed a slight increase in HA-staining (FIG. 9B). By 48 hours, the smooth muscle cells forming the neointima were strongly positive for HA (FIG. 9C), coincident with their expression of high levels of RHAMM (FIG. 9D). Between 7 and 14 days, the staining for HA decreased and became restricted to cells at the junction of the media and the neointima (FIG. 9D & E). Sections pretreated with hyaluronidase or preincubation of the biotinylated HA-binding probe with HA prevented staining (data not shown), confirming the specificity of the assay.

The RHAMM:HA Interaction Regulates Inflammatory Cell Chemotaxis

Figure 10:
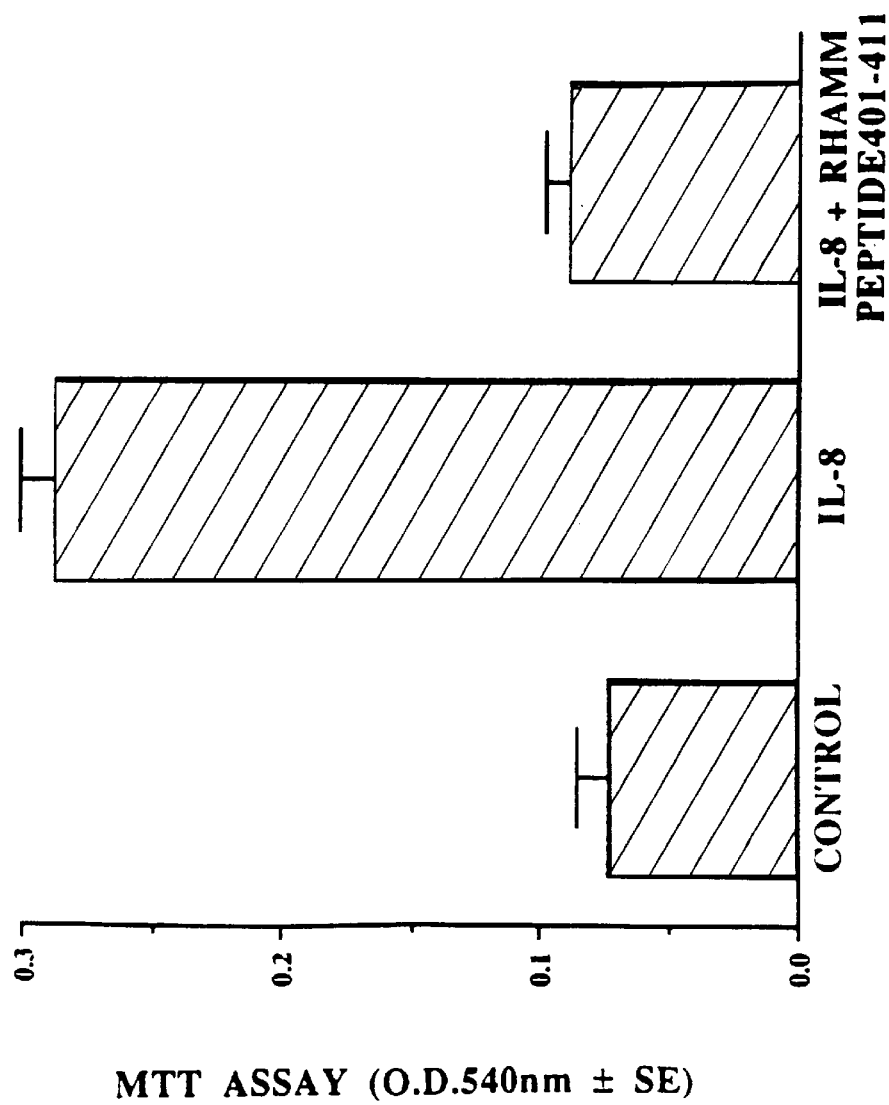
Figure 11:
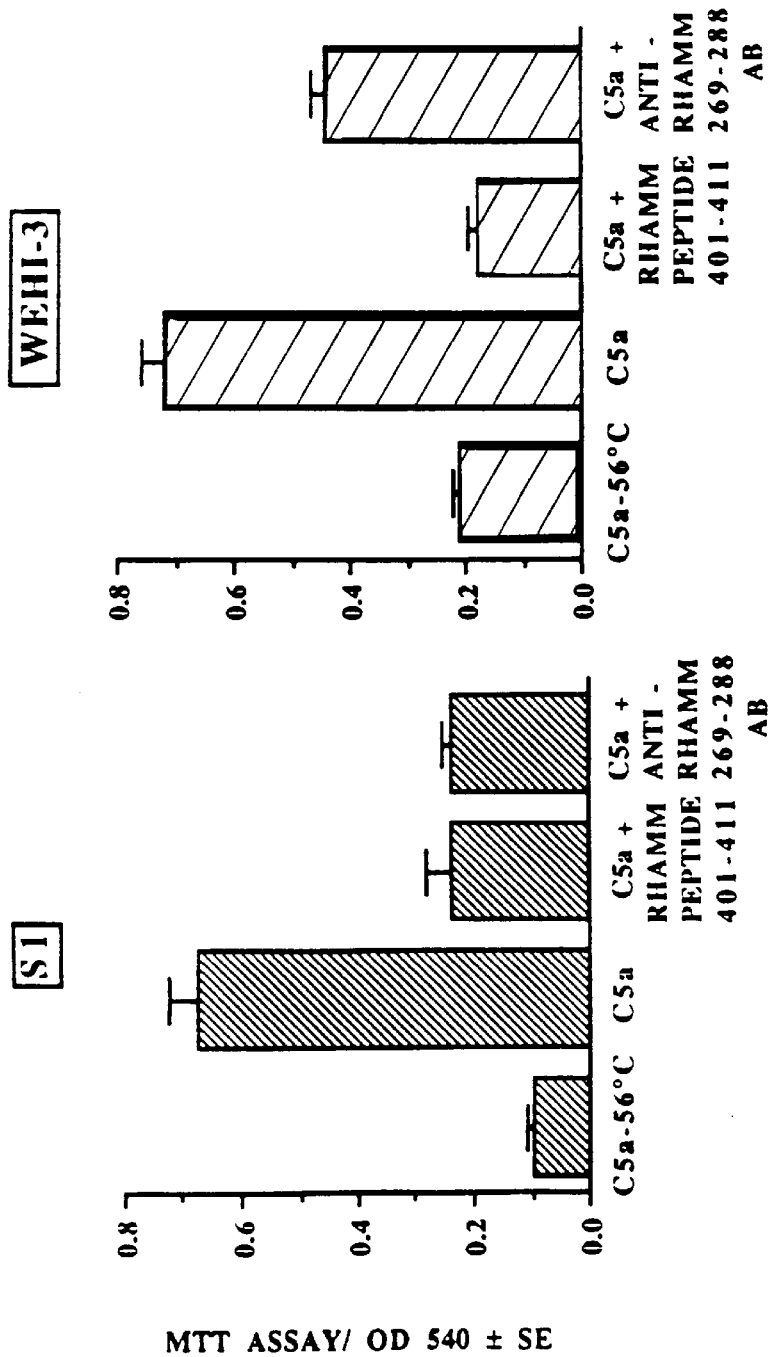

Since the expression of RHAMM was increased in the inflammatory cells adherent to the injury area of the carotid artery, the role of the RHAMM:HA interaction in neutrophil and macrophage chemotaxis was studied using both a peptide encoding one of the two HA-binding domains of RHAMM (aa$^{401-411}$)[14], and Anti-peptide aa$^{269-288}$ Ab previously shown to interfere with HA-binding to RHAMM (Ref. 14 and Savani et al., submitted). Human neutrophil chemotaxis to IL-8 was significantly inhibited by peptide aa$^{401-411}$ (FIG. 10), and both peptide aa$^{401-411}$ and Antipeptide aa$^{269-288}$ Ab inhibited the chemotaxis of the two human marcrophage cell lines S1 and WEHI-3, to endotoxin-activated mouse serum (FIG. 11).

The RHAMM:HA Interaction Regulates Smooth Muscle Cell Migration After Wounding Injury We have previously shown that Anti-RHAMM antisera inhibit the directional migration of smooth muscle cell monolayers into wounds (Savani et al., submitted). To further confirm the involvement of the RHAMM:HA interaction in this wounding response, we investigated the effect of a peptide encoding one of the HA-binding domains of RHAMM (aa$^{401-411}$)[14]. This peptide significantly reduced the rate of translocation of smooth muscle cells following wounding of monolayers (FIG. 12). A scrambled peptide containing the same amino acids as peptide aa$^{401-411}$ had no effect on the wounding response (FIG. 12).

Discussion

Hyaluronan, a component of the extracellular matrix, has been implicated in cell locomotion during embryogenesis[20, 21], tumor invasion[22], transformation by oncogenes[13], and in responses to injury[23-25]. The effect of HA on cell locomotion appears to be mediated by specific receptors[13,26] such as CD44[27] and RHAMM[14]. HA has been implicated in the migration of both endothelial and smooth muscle cells[28-30], and RHAMM has been shown to be important in the migration of embryonic smooth muscle cells[31] and of adult smooth muscle cells following wounding injury (Savani et al., submitted). Since smooth muscle cell migration forms a critical component of the pathogenesis of restenosis after balloon angioplasty[3], we hypothesized that the expression and distribution of RHAMM and HA would also play a role after balloon catheter de-endothelialization of rat carotid arteries in vivo.

Early accumulation of inflammatory cells at the denuded area of injured arteries has been described previously[32], and our results confirm these findings. The accumulation of inflammatory cells at sites injury requires their chemotactic migration to the site and subsequent adherence[33]. Adhesion is initiated by interaction with selections that leads to rolling of cells along the vessel wall, followed by strong adherence via specific vascular integrins, and subsequently extravastion (for review, see ref. 34). The increased expression of RHAMM in the inflammatory cells that are adherent to the denuded endothelium may perform several functions. The finding that both neutrophil and macrophage chemotaxis can be blocked using anit-RHAMM antisera or a peptide mimicking one of the HA-binding domains of RHAMM suggests that RHAMM:HA interactions may contribute to the accumulation of inflammatory cells at the injured site via chemotaxis. We have also shown that RHAMM:HA interactions regulate pseudopodal extension in fibroblasts, a process necessary for extravasation. Likely, RHAMM plays a role in this process during the extravasation of macrophages. We are currently investigating this possibility.

We have previously observed the constitutive expresson of a 65 kDa isoform of RHAMM by quiescent smooth muscle cell monolayers and the appearance of a 70 kDa isoform coincident with increased migration following wounding injury. This last protein has been predicted to represent a membrane form of RHAMM since its appearance coincides with increased immunofluorescence of membrane-localized RHAMM by FACS analysis (Savani et al., submitted). In the present study, we show that, like smooth muscle cells in vitro the uninjured carotid artery expressed a 65 kDa RHAMM and that following injury, a 70 kDa isoform appeared. This RHAMM isoform was only expressed between 36 and 72 hours after injury, and coincided with reports of the timeframe for migration of smooth muscle cells into the injured site[1,3]. A causal role of the RHAMM isoform is cell locomotion is currently being studied. Since an 84 kDa protein was not produced by smooth muscle cells in vitro, its nature and the cell type that expresses it are currently unknown.

We have previously shown increased association of HA with smooth muscle cell monolayers coincident with the membrane localization of RHAMM and the expression of the 70 kDa isoform following wounding injury (Savani et al., submitted). Increased staining for HA in the current study was in the time period of maximal migration and expression of the 70 kDa RHAMM isoform. These results support the hypothesis that RHAMM:HA interactions regulate cell motility. The ability of reagents that block RHAMM function in vitro, including anti-RHAMM antiserum and RHAMM peptide, is consitent with this proposal.

A number of growth factors, in particular PDGF-BB[35] and TGF-β1[36], have been implicated in smooth muscle cell migration, and in the pathogenesis of restenosis[6,7]. PDGF-BB, derived from both adherent platelets and from the smooth muscle cells themselves, has a greater effect on migration than on the proliferation of smooth muscle cells[6]. TGF-β1 is produced by the smooth muscle cells at the injured site and contributes to smooth muscle cell proliferation and abnormal extracellular matrix deposition in the latter stages of the restenotic process[7]. Growth factors have also been implicated in the regulation of inflammatory cell locomotion. Thus, TGF-β1 regulates the chemotaxis of monocytes[37]. Further, TGF-β1—stimulated increase in fibroblast locomotion is mediated by the RHAMM:HA interaction, and TGF-β1 regulates both the expression of RHAMM and the synthesis of HA in fibroblasts[38]. The regulation by TGF-β1 and PDGF-BB of RHAMM and HA expression in smooth muscle cells is currently under investigation.

Thus, in the present study, we have demonstrated that profound changes in expression of RHAMM and HA occur after in vivo vascular injury, and have shown that the RHAMM:HA interaction is required for inflammatory cell chemotaxis and smooth muscle cell migration in vitro. These data raise the possiblity of using agents that block RHAMM:HA interactions in vivo to reduce or prevent the development of restenosis after balloon catheter injury. These studies are currently being pursued in our laboratory.

Acknowledgments

This research was funded by the Medical Research Council of Canada (MRC), grant # 10948 (EAT), and the Manitoba Medical Services Foundation (RCS). EAT is the recipient of a Chilren's Hospital of Winnipeg Research Foundation Scholarship. The expert assistance of Ms. Elaine Garagon and Ms. Laurie Lange is gratefully appreciated.

REFERENCES

1. Ferns, G A A Stewart-Lee, A L and Änggård, E E: Arterial response to mechanical injury: balloon catheter de-endothelialization. Atherosclerosis 1992, 92:89–104
2. Ross, R: The pathogenesis of atherosclerosis: a perspective for the 1990's. Nature 1993, 362:801–809
3. Casscells, W: Migration of smooth muscle and endothelial cells: Critical events in restenosis. Circulation 1992, 86(3):723–729
4. Tanaka, Y, Adams, D H and Shaw, S: Proteoglycans on endothelial cells present adhesion-inducing cytokines to leukocytes. Immunol Today 1993, 14(3):111–115
5. Lövqvist, A. Emanuelsson, H, Nilsson, J, Lundqvist, H and Carlsson, J: Pathophysiological mechanisms for restenosis following coronary angioplasty: possible preventative alternatives. J Int Med 1993, 233:215–226
6. Jawien, A, Bowen-Pope, D F, Lindner, V, Schwartz, S M and Clowes, A W: Platelet-derived Growth Factor promotes smooth muscle cell migration and intimal thickening in a rat model of balloon angioplasty. J Clin Invest 1992, 89:507–511
7. Majesky, M W, Linder, V, Twardzik, D R, Schwartz, S M and Reidy, M A: Production of Transforming Growth Factor $β_1$ during repair of arterial injury. J Clin Invest 1991, 88:904–910
8. Rakugi, H, Jacob, H J, Krieger, J E, Ingelfinger, J R and Pratt, R E: Vascular injury induces aniotensinogen gene expression in the media and neointima. Circulation 1993, 87:283–290
9. Clowes, A W, Clowes, M M, Au, Y P T, Reidy, M A and Belin, D: Smooth muscle cells express urokinase during mitogenesis and tissue-type plasminogen activator during migration in injured rat carotid artery. Circ Res 1990, 67:61–67
10. Miano, J M, Vlasic, N, Tota, R R and Stemerman, M B: Smooth muscle cell immediate-early gene and growth factor activation follows vascular injury: A putative in vivo mechanism for autocrine growth. Arterioscler Thromb 1993, 13:211–219
11. Clowes, A W and Schwartz, S M: Significance of quiescent smooth muscle cell migration in the injured rat carotid artery. Circ Res 1985, 56:139–?
12. Clowes, A W, Reidy, M A and Clowes, M M: Mechanisms of stenosis after arterial injury. Lab Invest 1983, 49(2):208–215
13. Turley, E A, Austen, L, Vandeligt, K and Clary, C: Hyaluronan and a cell-associated hyaluronan binding protein regulate the locomotion of ras-transformed cells. J Cell Biol 1991, 112(5): 1041–1047
14. Hardwick, C, Hoare, K, Owens, R, Hohn, H P, Hook, M, Moore, D, Cripps, V, Austen, L, Nance, D M and Turley, E A: Molecular cloning of a novel Hyaluronan receptor that mediates tumor cell motility. J Cell Biol 1992, 117(6): 1343–1350
15. Yang, B, Zhang, L and Turley, E A: Identification of two hyaluronan-binding domains in the hyaluronan receptor RHAMM. J Biol Chem 1993, 268:8617–8623
16. Ripellino, J A, Killinger, M M, Margolis, R U and Margolis, R K: The hyaluronic acid binding region as a specific probe for the localization of hyaluronic acid in tissue sections. J Hisotchem Cytochem 1985, 33:1066–1086
17. Majack, R A and Clowes, A W: Inhibition of vascular smooth muscle cell migration by heparin-like glycosaminoglycans. J Cell Physiol 1984, 118:253–256
18. Stevenson, M M, Kongshovn, A L and Skamen, E: Genetic linkage of resistance to Listeria monocytogenes with macrophage inflammatory responses. J Immunol 1981, 127:402
19. Shi, Y, Kornovski, B S, Savani, R C and Turley, E A: A rapid, multiwell colormetric assay for chemotaxis. J Immunol Methods 1993, in press
20. Laurent, T C and Fraser, J R E: Hyaluronan FASEB J 1992, 6:2397–2404
21. Toole, B P: Developmental role of hyaluronate, Conn Tiss Res 1982, 10:93–100
22. Turley, E A: Hyaluronan and cell locomotion. Cancer Met Rev 1992, 11:21–30
23. Waldenström, A, Martinussen, H J, Gerdin, B and Hällgren, R: Accumulation of hyaluronan and tissue edema in experimental myocardial infarction. J Clin Invest 1991, 88:1622–1628
24. Weigel, P H, Fuller, G M and LeBoeuf, R D: A model for the role of hyaluronic acid and fibrinogen in the early events of inflammatory response and wound healing. J Theoret Biol 1986, 119:219–234
25. Bray, B A, Sampson, P M, Osman, M, Giandomenico, A and Turino, G M: Early changes in lung tissue hyaluronan (hyaluronic acid) and hyaluronidase in bleomycin-induced alveolitis in hamsters. Am Rev Resp Dis 1991, 143:284–288
26. Toole, B P: Hyaluronan and its binding proteins, the hyaladherins. Curr Opn Cell Biol 1990, 2:839–844
27. Haynes, B F, Liao, H-X and Patton, K L: The transmembrane hyaluronate receptor (CD44): multiple functions, multiple forms. Cancer Cells 1991, 3(9): 347–350
28. Ausprunk, D H, Boudreau, C L and Nelson, D A: Proteoglycans in the microvasculature II: Histochemical localization in proliferating capillaries of the rabbit cornea. Am J Pathol 1981, 103:367–375
29. West, D C and Kumar, S: The effect of hyaluronate and its oligosaccharides on endothelial cell proliferation and monolayer integrity. Exp Cell Res 1989, 183:179–196
30. Boudreau, N and Rabinovitch, M: Developmentally regulated changes in extracellular matrix in endothelial and smooth Muscle Cells in the ductus arteriosus may be related to intimal proliferation. Lab Invest 1991, 64(2): 187–199
31. Boudreau, N, Turley, E A and Rabinovitch, M: Fibronectin, Hyaluronan, and a Hyaluronan Binding Protein contribute to increased ductus arteriosus smooth muscle cell migration. Develop Biol 1991, 143:235–247

32. Kockx, M M, De Meyer, G R Y, Jacob, W A, Bult, H and Herman, A G: Triphasic sequence of neointimal formation in the cuffed carotid artery of the rabbit. Arteriosci Thromb 1992, 12:1447–1457
33. Lasky, L A: Selections: Interpreters of cell-specific carbohydrate information during inflammation. Science 1992, 258:964–969
34. Dustin, M L and Springer, T A: Annu Rev Immunol 1991, 9:27–66
35. Welsh, C J, Schmieichel, K and McBride, K: Platelet-Derived Growth Factor activates Phospholipase D and chemotactic responses in vascular smooth muscle cells. In Vitro Cell Dev Biol 1991, 27A:425–431
36. Merwin, J R, Roberts, A, Kondaiah, P, Tucker, A and Madri, J A: Vascular cell responses to TGF-$\beta_3$ mimic those TGF-$\beta_1$ in vitro. Growth Factors 1991, 5(149–158)
37. Wahl, S M, Hunt, D A, Wakefield, L M, McCartney-Francis, N, Wahl, L M; Roberts, A B and Spom, M B: Transforming growth factor type beta induces monocyte chemotaxis and growth factor production. Proc Natl Acad Sci, U.S.A. 1987, 84 (August 1987):5788–5792
38. Samuel, S K, Hurta, R A R, Spearman, M A, Wright, J A, Turley, E A and Greenberg, A H: TGF-$\beta_1$ stimulation of cell locomotion is mediated by the hyaluronan receptor RHAMM and hyaluronan. J Cell Biol 1993, in press.

The Embodiments of the invention in which an exclusive property or privilege is claimed are as follows:

1. A method of inhibiting the narrowing of the vascular tubular walls of an animal by the proliferation of endothelial cells in the area of trauma after the vascular tubular walls have been traumatized, the method comprising the administration of a therapeutically effective non-toxic amount of a form of hyaluronic acid selected from the group consisting of hyaluronic acid and pharmaceutically acceptable salts thereof, and a therapeutically effective amount of an agent selected from the group consisting of a non-steroidal anti-inflammatory drug (NSAID), Vitamin C, a stenosis inhibiting drug, an anti-oxidant, a free radical scavenger and combinations thereof for enhancing the effect of the form of hyaluronic acid administered in the inhibition of the narrowing of the tubular walls to the animal to inhibit the narrowing of the vascular tubular walls by the proliferation of the endothelial cells on the area of trauma, and wherein the molecular weight of the form of hyaluronic acid is less than 750,000 daltons and greater than 150,000 daltons.

2. The method of claim 1, wherein the molecular weight of the form of hyaluronic acid is greater than 150,000 daltons and less than 225,000 daltons.

3. The method of claim 2, wherein the tubular walls are arteries which have been subjected to balloon angioplasty and the administration takes places before, during or after the balloon angioplasty.

4. The method of claim 3 wherein the amount of the form of hyaluronic acid administered is between 10 mg and 3000 mg.

5. A method of inhibiting arterial restenosis of the arterial wall by the proliferation of endothelial cells on the inner wall of the artery after balloon angioplasty in a human, the method comprising the administration of a therapeutically effective non-toxic amount of a form of hyaluronic acid selected from the group consisting of hyaluronic acid, pharmaceutically acceptable salts thereof and combinations thereof, a therapeutically effective amount of an agent selected from the group consisting of a non-steroidal anti-inflammatory drug (NSAID), Vitamin C, a stenosis inhibiting drug, an anti-oxidant, a free radical scavenger and combinations thereof for enhancing the effect of the form of hyaluronic acid administered in the inhibition of the narrowing of the tubular walls to the human to inhibit arterial restenosis by the proliferation of endothelial cells on the inner wall of the artery, and wherein the molecular weight of the form of hyaluronic acid is less than 750,000 daltons and greater than 150,000 daltons.

6. The method of claim 5, wherein the molecular weight of the form of hyaluronic acid is greater than 150,000 daltons and less than 225,000 daltons.

7. The method of claim 5, wherein the amount of the form of hyaluronic acid administered is between 10 mg and 3000 mg.

8. The method of claim 5, 6, or 7 wherein the form of hyaluronic acid is administered prior to, during or after the balloon angioplasty.

9. The method of claim 1, 2, 3, 4, 5, 6, or 7 wherein the form of hyaluronic acid is sodium hyaluronate administered intravenously.

10. The method of claim 1, 2, 3, 4, 5, 6 or 7 wherein the therapeutically effective amount of the combination of the form of hyaluronic acid and agent are in the form for intravenous administration.

11. A method of inhibiting arterial restenosis of the arterial wall by the proliferation of endothelial cells on the area of trauma after balloon angioplasty, the method comprising the administration of a therapeutically effective non-toxic amount of hyaluronic acid and/or pharmaceutically acceptable salts thereof whose molecular weight is less than 750,000 daltons and greater than 150,000 daltons, and a therapeutically effective amount of an agent selected from the group consisting of a non-steroidal anti-inflammatory drug (NSAID), Vitamin C, a stenosis inhibiting drug, an anti-oxidant, a free radical scavenger and combinations thereof for enhancing the effect of the form of hyaluronic acid administered in the inhibition of the narrowing of the tubular walls to inhibit arterial restenosis by the proliferation of the endothelial cells on the area of trauma.

12. The method of claim 11, wherein the amount of the hyaluronic acid and/or salts thereof administered is between 10 mg and 3000 mg.

13. The method of claim 12 wherein the NSAID is an effective dosage amount and the amount of hyaluronic acid and salts thereof exceeds 200 mg.

14. A pharmaceutical composition comprising together with diluents, adjuvants and other pharmaceutical carriers as desired;

(1) an effective amount of a form of hyaluronic acid selected from the group consisting of hyaluronic acid, pharmaceutically acceptable salts thereof, and combinations thereof, and (2) an agent selected from the group consisting of a stenosis inhibiting drug, a non-steroidal anti-inflammatory drug (NSAID), Vitamin C, a free radical scavenger, and an anti-oxidant and combinations thereof, for inhibiting the narrowing of the vascular tubular walls of an animal by the build-up of endothelial cells on the vascular tubular walls after the tubular walls have been traumatized, the composition being characterized by an effective non-toxic amount of the form of hyaluronic acid being incorporated into the composition together with a therapeutically effective amount of agent (2), to inhibit tubular wall narrowing by the build-up of endothelial cells on the vascular tubular walls, wherein the effective amount of component (1) is between 10 mg to 3000 mg to prevent the narrowing of the tubular walls of the animal by the build-up of endothelial cells on the vascular tubular walls and wherein component (2) enhances the effect of component (1) in the prevention of the narrowing of the tubular walls by the build-up of endothelial cells on the vascular tubular walls, and wherein the molecular weight of component (1) is less than 750,000 daltons and greater than 150,000 daltons.

15. The composition of claim 14 wherein the molecular weight of component (1) is greater than 150,000 daltons and less than 225,000 daltons.

16. The composition of claim 14 or 15 wherein component (1) comprises a stenosis-inhibiting drug and an NSAID.

17. The composition according to claim 14 or 15 in injectable or intravenous form and component (1) is sodium hyaluronate.

18. The method of claim 14 or 15, wherein component (1) is utilized at a dose between 10 mg to 1000 mg.

19. The composition of claim 14 or 15, wherein the amount of component (1) is greater than 200 mg.

20. The composition of claim 19 wherein the pharmaceutical composition is for inhibition of arterial restenosis after balloon angioplasty in humans.

* * * * *